(12) United States Patent
Koyama et al.

(10) Patent No.: US 11,571,197 B2
(45) Date of Patent: Feb. 7, 2023

(54) IN-TUBE TRANSIT OBJECT

(71) Applicants: Mikuro Spring Co., Ltd., Suwa (JP); GUNZE LIMITED, Ayabe (JP)

(72) Inventors: Takayuki Koyama, Suwa (JP); Makoto Natori, Suwa (JP); Yusuke Sato, Suwa (JP); Saki Okumura, Ayabe (JP); Yuuki Kato, Ayabe (JP); Mieko Ishikawa, Ayabe (JP)

(73) Assignees: Mikuro Spring Co., Ltd., Suwa (JP); GUNZE LIMITED, Ayabe (JP)

( * ) Notice: Subject to any disclaimer, the term of this patent is extended or adjusted under 35 U.S.C. 154(b) by 240 days.

(21) Appl. No.: 17/113,794

(22) Filed: Dec. 7, 2020

(65) Prior Publication Data
US 2021/0177388 A1 Jun. 17, 2021

(30) Foreign Application Priority Data

Dec. 17, 2019 (JP) .............................. JP2019-227260
Oct. 26, 2020 (JP) .............................. JP2020-178687

(51) Int. Cl.
*A61B 17/00* (2006.01)

(52) U.S. Cl.
CPC .... *A61B 17/0057* (2013.01); *A61B 17/00234* (2013.01); *A61B 2017/00004* (2013.01); *A61B 2017/00243* (2013.01); *A61B 2017/00592* (2013.01); *A61B 2017/00606* (2013.01); *A61B 2017/00623* (2013.01); *A61B 2017/00646* (2013.01)

(58) Field of Classification Search
CPC .......... A61B 17/00234; A61B 17/0057; A61B 2017/00004; A61B 2017/00243; A61B 2017/00575; A61B 2017/00592; A61B 2017/00606; A61B 2017/00623; A61B 2017/00646; A61B 2017/12054; A61B 2017/12095; A61B 2090/3966

See application file for complete search history.

(56) References Cited

U.S. PATENT DOCUMENTS

2007/0250081 A1* 10/2007 Cahill ................ A61B 17/0057
606/151

FOREIGN PATENT DOCUMENTS

JP          2019-17795 A      2/2019
WO     WO-2016/174972 A1   11/2016

* cited by examiner

*Primary Examiner* — Mohamed G Gabr
(74) *Attorney, Agent, or Firm* — Leason Ellis LLP; Melvin C. Garner; Mitsuhiro Haraguchi

(57) ABSTRACT

An in-tube transit object that is inserted in a tube includes: a coil section formed by winding a wire; and a fiber section attached to an end on one side and an end on the other side in a winding-axis direction of the coil section. The coil section is formed with a large diameter section, through which fiber of the fiber section is inserted, at the end on the one side and the end on the other side, and is inserted in an extending state in the winding-axis direction when the in-tube transit object is inserted into the tube. The fiber section is configured to expand when seen in the winding-axis direction in the case where the in-tube transit object is inserted in the tube and then discharged from the tube, which brings the coil section into a compressed state in the winding-axis direction.

14 Claims, 22 Drawing Sheets

IN-TUBE TRANSIT OBJECT

This application claims the benefit of priority to Japanese Patent Applications No. 2019-227260 filed on Dec. 17, 2019, and No. 2020-178687 filed on Oct. 26, 2020, the contents of which are incorporated herein by reference in their entireties.

FIELD OF THE INVENTION

The present invention relates to an in-tube transit object.

BACKGROUND OF THE INVENTION

Conventionally, various objects are used as in-tube transit objects, each of which is inserted in a tube. Of these, there is an object configured that a part of the in-tube transit object expands in association with discharge of the in-tube transit object from inside of the tube after the in-tube transit object is inserted in the tube. For example, in Japanese Patent Application Publication 2019-17795, a closing plug (a defective hole closing member) that is inserted in a catheter is disclosed. The closing plug in Japanese Patent Application Publication 2019-17795 has a coil spring and is configured to compress the coil spring so as to be able to expand a first cylindrical section and a second cylindrical section, each of which is formed from a bioabsorbable fiber, in association with the discharge of the closing plug from the catheter after the closing plug is inserted in the catheter.

CONVENTIONAL ART DOCUMENT

Japanese Patent Application Publication 2019-17795 (JP 2019-17795A)

Technical Problem

In the closing plug disclosed in Japanese Patent Application Publication 2019-17795, the bioabsorbable fiber is engaged with both ends in an axial direction of the coil spring. However, although a detailed configuration is not described in Japanese Patent Application Publication 2019-17795, in the in-tube transit object that includes a fiber section attached to an end on one side and an end on the other side in a winding-axis direction of a coil section and is configured that the fiber section expands in association with the discharge of the in-tube transit object from the tube after the in-tube transit object is inserted in the tube, an attachment configuration between the fiber section and the coil section tends to be complicated. In the case where a fiber in the fiber section is simply wound around an element wire constituting the coil section, there is such a problem that an attachment position of the fiber is displaced. Thus, the coil section has to be provided with a dedicated attachment section to which the fiber in the fiber section is attached.

In view of the above, the present invention has a purpose of providing an in-tube transit object having a simple configuration that a fiber section expands in association with discharge of the in-tube transit object from a tube after the in-tube transit object is inserted in the tube.

SUMMARY OF THE INVENTION

Solution to Problem

An in-tube transit object according to a first aspect of the present invention for solving the above problem is an in-tube transit object that is inserted in a tube, and includes: a coil section formed by winding an element wire; and a fiber section attached to an end on one side and an end on the other side in a winding-axis direction of the coil section. The coil section is formed with hole formed sections, through each of which fiber of the fiber section is inserted, at the end on the one side and the end on the other side, and is inserted in an extending state in the winding-axis direction at the time when the in-tube transit object is inserted in the tube. The fiber section is configured to expand when seen in the winding-axis direction in the case where the in-tube transit object is inserted in the tube and then discharged from the tube, which brings the coil section into a compressed state in the winding-axis direction.

According to this aspect, the hole formed section, through which the fiber is inserted, is formed at the end on the one side and the end on the other side in the winding-axis direction of the coil section. Accordingly, when the fiber is inserted through the hole formed section, which can easily be formed, it is possible to suppress an attachment position of the fiber from being displaced. Therefore, it is possible to easily create such a configuration that the fiber section expands in association with discharge of the in-tube transit object from the tube after insertion of the in-tube transit object in the tube.

In the first aspect, in an in-tube transit object according to a second aspect of the present invention, the hole formed section is a large diameter section that is formed by increasing a winding diameter of the element wire to be larger than winding diameters of the other portions in the coil section.

According to this aspect, the large diameter section, through which the fiber is inserted, is formed at the one end and the end on the other side in the winding-axis direction of the coil section. Therefore, the large diameter section can be formed as a portion to which the fiber is attached by the simple method for increasing the winding diameter of the element wire.

In the second aspect, in an in-tube transit object according to a third aspect of the present invention, the coil section is formed with the large diameter section such that a hole section, through which the fiber is inserted, is formed at plural positions when the coil section is seen in the winding-axis direction.

According to this aspect, the coil section is formed with the large diameter section such that the hole section, through which the fiber is inserted, is formed at the plural positions when the coil section is seen in the winding-axis direction. Therefore, compared to a configuration that the hole section, through which the fiber is inserted, is only formed at one position, the fiber section can further reliably be attached to the coil section.

In the second aspect, in an in-tube transit object according to a fourth aspect of the present invention, the coil section is formed with the plural large diameter sections in a manner to overlap each other when the coil section is seen in the winding-axis direction.

According to this aspect, the coil section is formed with the plural large diameter sections in the manner to overlap each other when the coil section is seen in the winding-axis direction. Accordingly, the single fiber can be inserted in the plural hole sections of the plural large diameter sections. Therefore, it is possible to increase strength of portions, through each of which the fiber is inserted.

In the first aspect, in an in-tube transit object according to a fifth aspect of the present invention, the coil section is made of metal.

According to this aspect, since the coil section is made of metal, the coil section can have high strength.

In the fifth aspect, an in-tube transit object according to a sixth aspect of the present invention, the coil section is made from an alloy containing nickel and titanium.

According to this aspect, the coil section is made from the alloy containing nickel and titanium. The alloy containing nickel and titanium is especially superior in biological compatibility, and thus can particularly favorably be used in the medical field and the like, for example.

In the first aspect, in an in-tube transit object according to a seventh aspect of the present invention, the tube is a catheter.

According to this aspect, the in-tube transit object for the catheter can easily be provided with such a configuration that the fiber section expands in association with the discharge of the in-tube transit object from the tube after the insertion of the in-tube transit object in the tube.

In the seventh aspect, in an in-tube transit object according to an eighth aspect of the present invention, the coil section has an attachment/detachment section to/from a wire that is inserted through the catheter, the wire has a rotatable male screw at a tip, and the attachment/detachment section has as a female screw that is formed on inside of the coil section and corresponds to the male screw.

According to this aspect, the attachment/detachment section is formed to have the inside of the coil section as the female screw. Therefore, the attachment/detachment section can easily be formed.

In the eighth aspect, in an in-tube transit object according to a ninth aspect of the present invention, the attachment/detachment section has a tubular section that covers an outer circumference of the female screw.

According to this aspect, the attachment/detachment section has the tubular section that covers the outer circumference of the female screw. Therefore, it is possible to suppress the coil section from expanding radially. In addition, it is possible to suppress the female screw of the attachment/detachment section as the coil section from failing to play a role as the female screw due to radial expansion of the attachment/detachment section when the male screw is threaded to the attachment/detachment section.

In the ninth aspect, in an in-tube transit object according to a tenth aspect of the present invention, the tubular section covers the outer circumference of the female screw from the end on the one side to the end on the other side.

In the case where a distance from the end on the one side to the end on the other side in the coil section is increased, it becomes difficult to rigidly fix the tubular section to the coil section. However, according to this aspect, the tubular section covers the outer circumference of the female screw from the end on the one side to the end on the other side. Therefore, the tubular section can firmly be fixed to the coil section.

In the seventh aspect, an in-tube transit object according to an eleventh aspect of the present invention has an attachment/detachment section that is fixed to the coil section and can be attached/detached to/from a wire inserted through the catheter. The attachment/detachment section is provided with a penetrating section, through which a string-shaped member is inserted, and is fixed to the end of the coil section at the time when the string-shaped member is inserted through the penetrating section and is also inserted through the hole formed section. The wire has a rotatable male screw at a tip. The attachment/detachment section has a female screw that corresponds to the male screw.

According to this aspect, the attachment/detachment section that has the female screw corresponding to the male screw of the wire and that is fixed to the end of the coil section by the string-shaped member by using the hole formed section. Therefore, with the attachment/detachment section having the simple configuration in which fitting accuracy of the screw to the wire is high, the coil section can be attached/detached to/from the wire.

In the eleventh aspect, an in-tube transit object according to a twelfth aspect of the present invention, the wire is inserted through the coil section from the end on the one side to the end on the other side and is connected to the attachment/detachment section.

According to this aspect, the wire is inserted through the coil section from the end on the one side to the end on the other side and is connected to the attachment/detachment section. Thus, the coil section is reinforced from the inside by the wire. Therefore, it is possible to suppress bending of the coil section in the catheter and to improve an insertion property of the wire in the catheter.

In the eleventh aspect, in an in-tube transit object according to a thirteenth aspect of the present invention, the string-shaped member is formed by using a radiopaque material.

According to this aspect, the string-shaped member is formed by using the radiopaque material. Therefore, it is possible to improve visibility of the in-tube transit object 1 in this embodiment at the time when an X-ray is used at a medical site.

In the first aspect, an in-tube transit object according to a fourteenth aspect of the present invention, the fiber section is configured to expand at two positions on the end side on the one side and the end side on the other side when seen in the winding-axis direction in the case where the in-tube transit object is inserted in the tube and then discharged from the tube, which brings the coil section into the compressed state in the winding-axis direction.

According to this aspect, the fiber section is configured to expand at the two positions on the end side on the one side and the end side on the other side. Therefore, it is possible to close a target hole by arranging the fiber section in a manner to hold the hole at the two positions at the time when the fiber section is discharged from the tube.

DETAILED DESCRIPTION OF THE INVENTION

Figure 1:
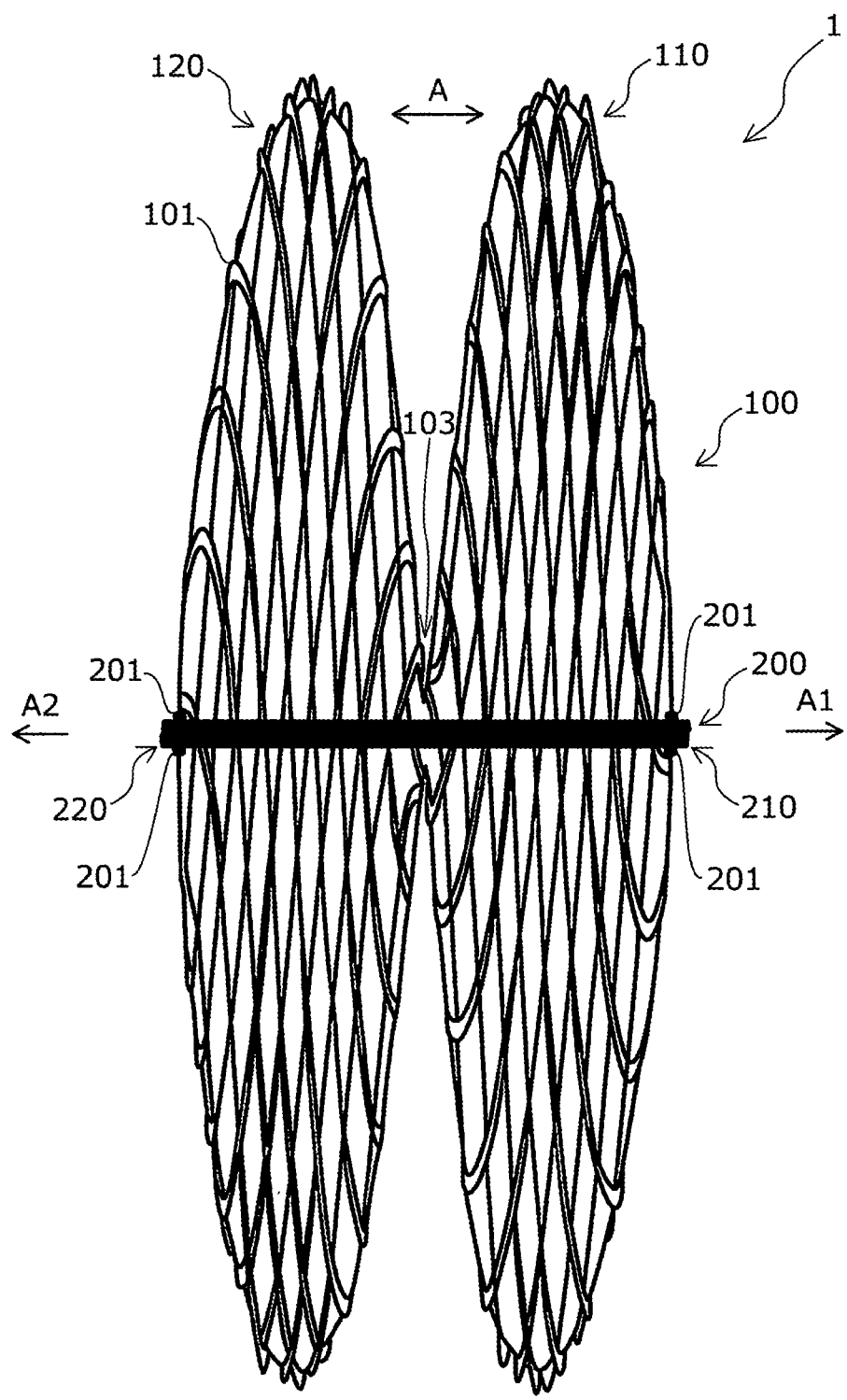
FIG. 1 is a schematic view illustrating an in-tube transit object according to a first embodiment of the present invention and a state where a coil spring is compressed.

[First Embodiment] (FIG. 1 to FIG. 12)

A detailed description will hereinafter be made on an in-tube transit object 1 according to an embodiment of the present invention with reference to the accompanying drawings. A description will firstly be made on the in-tube transit object 1 according to a first embodiment. The in-tube transit object 1 of this embodiment is an in-tube transit object that is inserted in a catheter as a tube, and is a defective hole closing member that can be used for catheterization for a patient with an atrial septal defect. However, the in-tube transit object according to the present invention is not limited to the defective hole closing member. The in-tube transit object according to the present invention may be an in-tube transit object that can be used for the catheterization for a patient with a defect other than the atrial septal defect, or may further be an in-tube transit object inserted in a tube for industrial application, for example. Such a tube differs from a tube for medical application such as the catheter. In FIG. 1 to FIG. 4 and FIG. 6 to FIG. 9, a pipe 240 that is fitted to an end 210 of a coil spring 200 is not illustrated.

Furthermore, in the following embodiment, a description will be made that an interwoven composition of the in-tube transit object 1 organizes a bioabsorbable fiber (one example of a wiring material). However, the present invention is not limited thereto. In the case where the in-tube transit object 1 is used for the catheterization, the in-tube transit object 1 is preferably a defective hole closing member that can be used to perform the catheterization for closing a defective hole formed in a living body. However, the interwoven composition thereof may be constructed of the wiring material other than the bioabsorbable fiber. Such a wiring material preferably has a certain degree of hardness in order to have a shape-retaining property (a form-retaining property).

(Overall Configuration of In-Tube Transit Object)

As illustrated in FIG. 1 to FIG. 5 and the like, the in-tube transit object 1 includes a cylindrical body 100 having an interwoven composition, for which a wiring material 101 formed from a bioabsorbable fiber is used. A cylindrical diameter of a substantially center portion 103 of the cylindrical body 100 is smaller than cylindrical diameters of the other portions. The cylindrical body 100 includes: a first cylindrical section 110 on a direction A1 side of a longitudinal direction A of the cylindrical body 100 with the substantially center portion 103 being a reference; and a second cylindrical section 120 on a direction A2 side of the longitudinal direction A of the cylindrical body 100 with the substantially center portion 103 being the reference.

Figure 10:
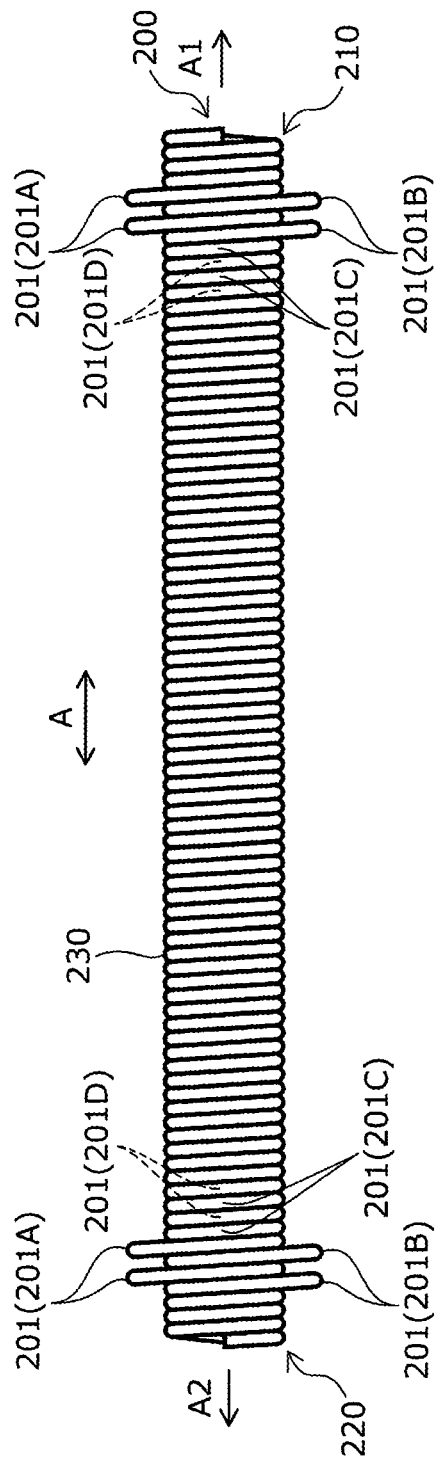
FIG. 10 is a schematic view in which the coil spring of the in-tube transit object in FIG. 1 is seen from a direction that crosses a winding-axis direction.
Figure 11:
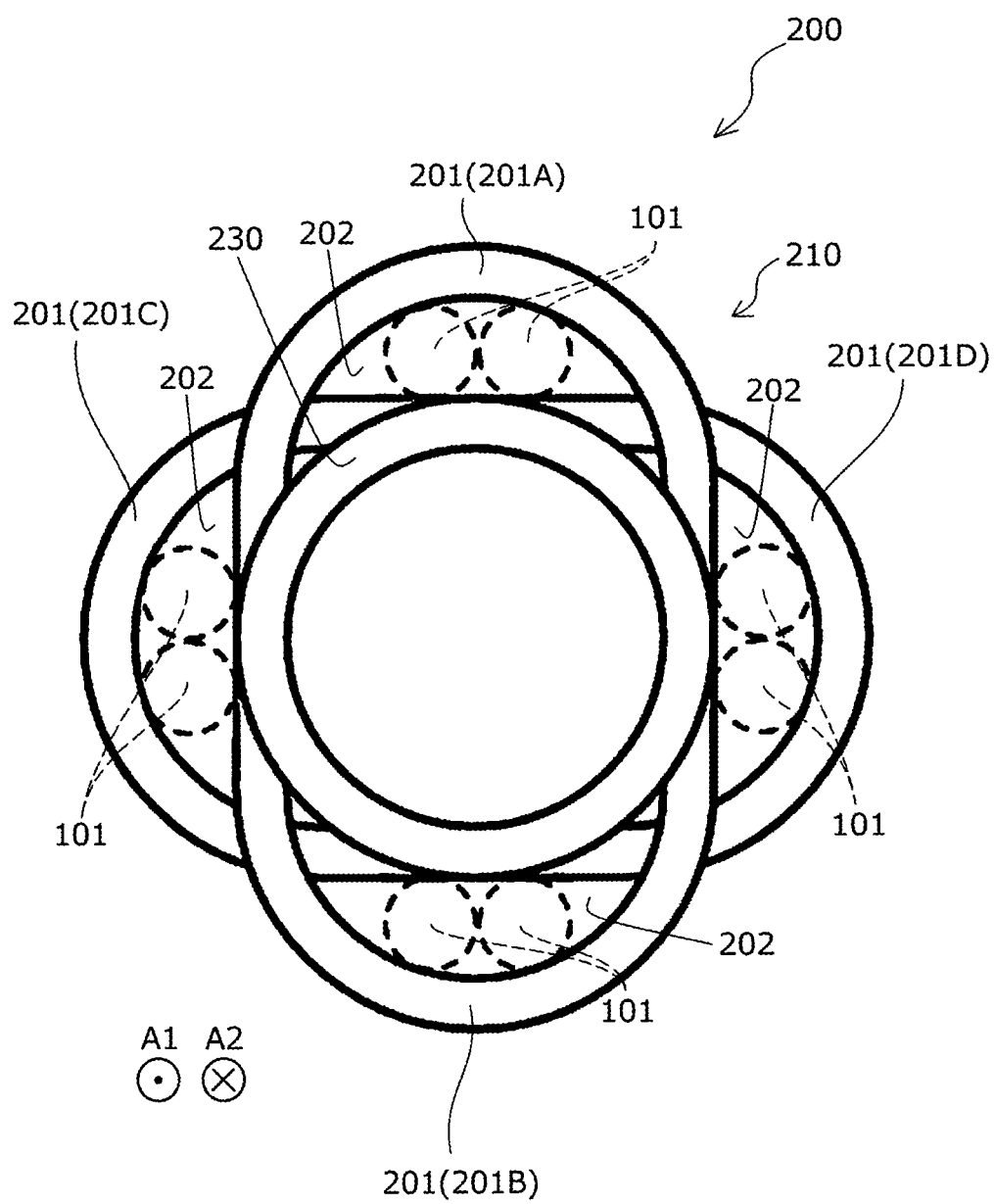
FIG. 11 is a schematic view in which the coil spring of the in-tube transit object in FIG. 1 is seen in the winding-axis direction.

In addition, as illustrated in FIG. 1 to FIG. 5 and the like, the in-tube transit object 1 includes the coil spring 200 in the cylindrical body 100. In the coil spring 200, the longitudinal direction A of the cylindrical body 100 is set as a winding-axis direction of an element wire 230 (see FIG. 5 and FIG. 10). A detailed description on a configuration of the coil spring 200 will be made below. As illustrated in FIG. 10, FIG. 11, and the like, the coil spring 200 has large diameter sections 201 at the end 210 on the direction A1 side and at an end 220 on the direction A2 side. A winding diameter of each of the large diameter sections 201 is larger than winding diameters of the other portions.

The wiring material 101 at the end on the direction A1 side of the first cylindrical section 110 in the cylindrical body 100 is inserted in a hole section 202 (see FIG. 11), which is formed when the large diameter section 201 is formed in the coil spring 200. With such a configuration, the first cylindrical section 110 is attached to the coil spring 200. Similarly, the wiring material 101 at the end on the direction A2 side of the second cylindrical section 120 in the cylindrical body 100 is inserted in the hole section 202, which is formed when the large diameter section 201 is formed in the coil spring 200. With such a configuration, the second cylindrical section 120 is attached to the coil spring 200.

Here, FIG. 1 illustrates a state where the coil spring 200 is compressed in the in-tube transit object 1 of this embodiment. In the case where the in-tube transit object 1 of this embodiment is in a state of not being inserted in a tube such as a catheter 300 (see FIG. 3) and is not applied with a force from the outside, the coil spring 200 generates a compressive force by a spring pressure thereof in the longitudinal direction A of the cylindrical body 100, and thus is brought into a state as illustrated in FIG. 1. The wiring material 101 of the cylindrical body 100 is woven such that, when the coil spring 200 is compressed, both of the first cylindrical section 110 and the second cylindrical section 120 expand in a direction that crosses the longitudinal direction A of the cylindrical body 100.

Figure 2:
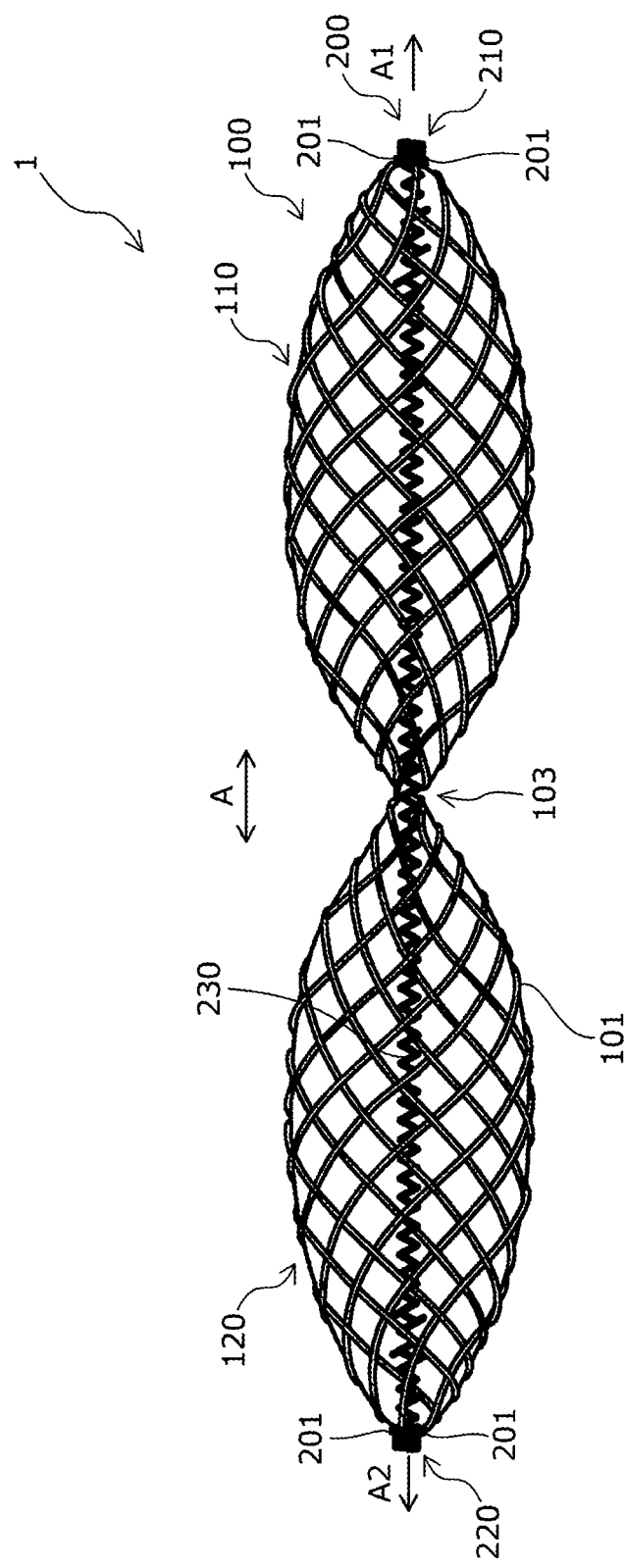
FIG. 2 is a schematic view illustrating the in-tube transit object in FIG. 1 and a state where the coil spring expands from the state in FIG. 1.
Figure 3:
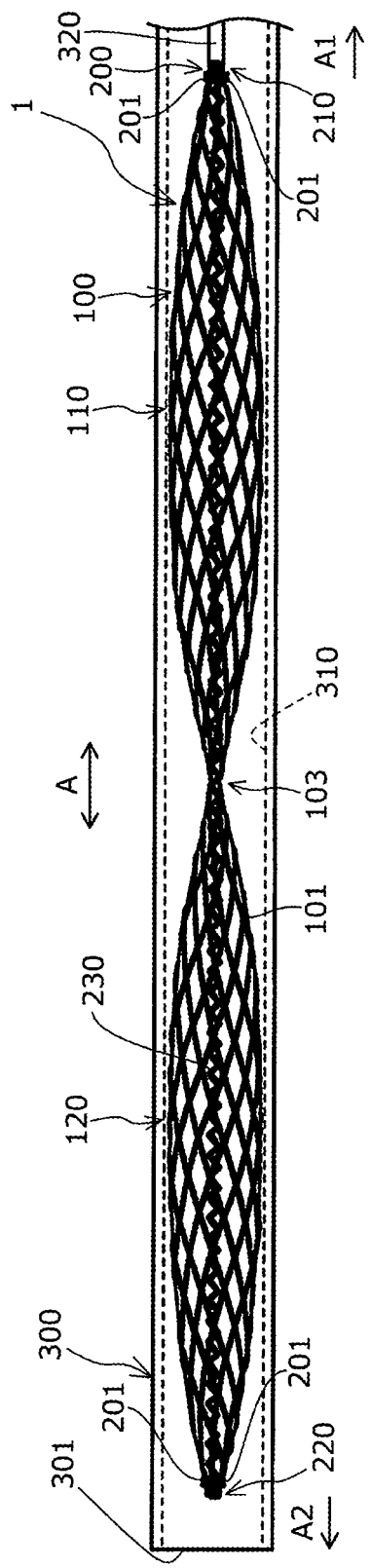
FIG. 3 is a schematic view illustrating the in-tube transit object in FIG. 1, a state where the in-tube transit object is in a catheter, and a state where the coil spring further expands from the state in FIG. 2.

Then, as illustrated in FIG. 2, when the coil spring 200 extends along the longitudinal direction A of the cylindrical body 100 from the state illustrated in FIG. 1, both of the first cylindrical section 110 and the second cylindrical section 120 are deformed in a manner to be narrowed in the direction that crosses the longitudinal direction A of the cylindrical body 100 in comparison with the state illustrated in FIG. 1. When the in-tube transit object 1 is introduced into the catheter 300, for example, and the coil spring 200 is thereby brought into a further expanding state along the longitudinal direction A of the cylindrical body 100 from the state illustrated in FIG. 2, as illustrated in FIG. 3, both of the first cylindrical section 110 and the second cylindrical section 120 are deformed in the manner to be further narrowed in the direction that crosses the longitudinal direction A of the cylindrical body 100 in comparison with the state illustrated in FIG. 2. In other words, when the in-tube transit object 1 is inserted in the tube such as the catheter 300, and the cylindrical body 100 is thereby deformed in a manner to be narrowed in the direction that crosses the longitudinal direction A of the cylindrical body 100, the coil spring 200 is brought into the expanding state along the longitudinal direction A of the cylindrical body 100.

Figure 4:
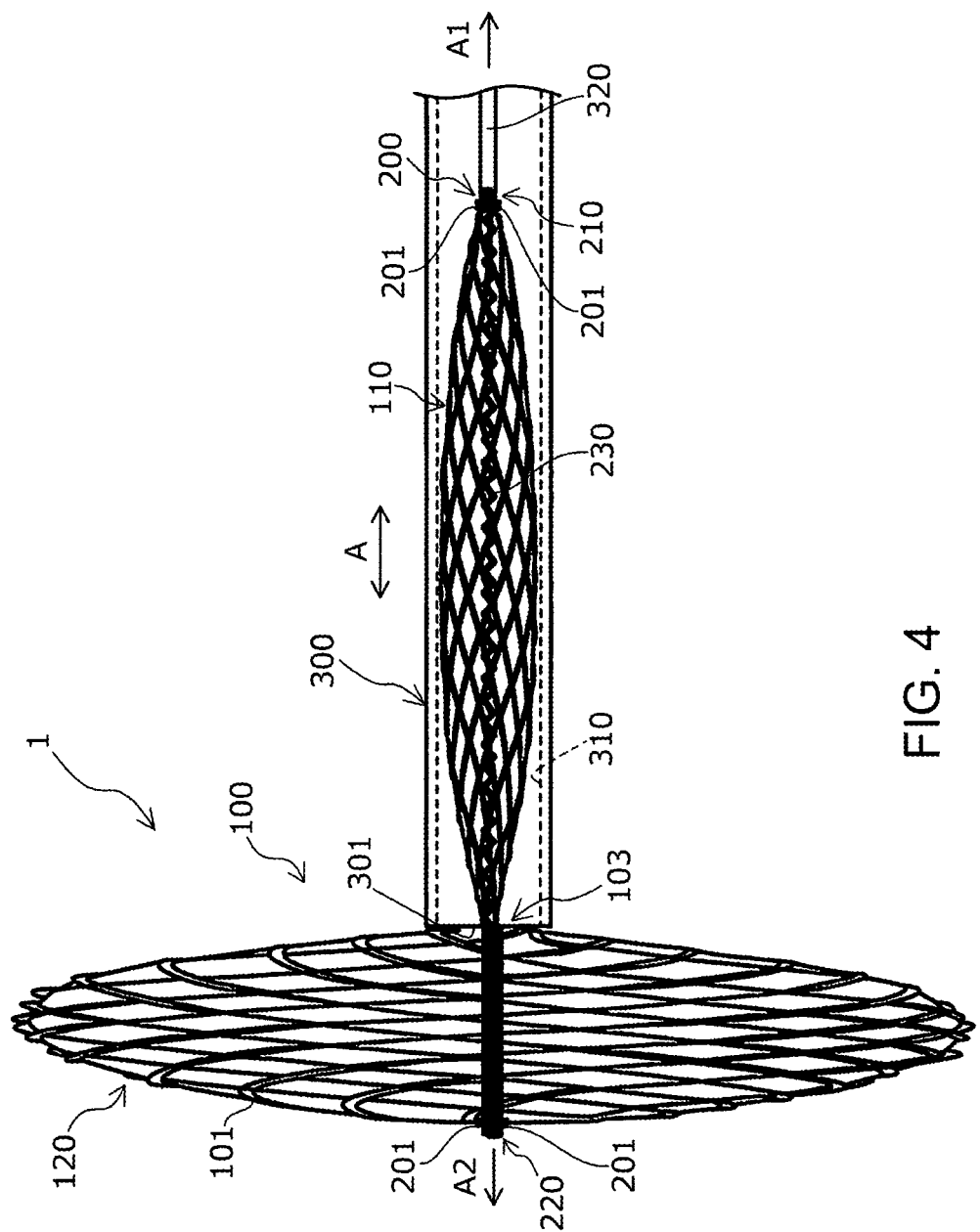
FIG. 4 is a schematic view illustrating the in-tube transit object in FIG. 1, a state where the in-tube transit object is partially discharged from the catheter, and a state where a portion of the coil spring discharged from the catheter is compressed.
Figure 5:
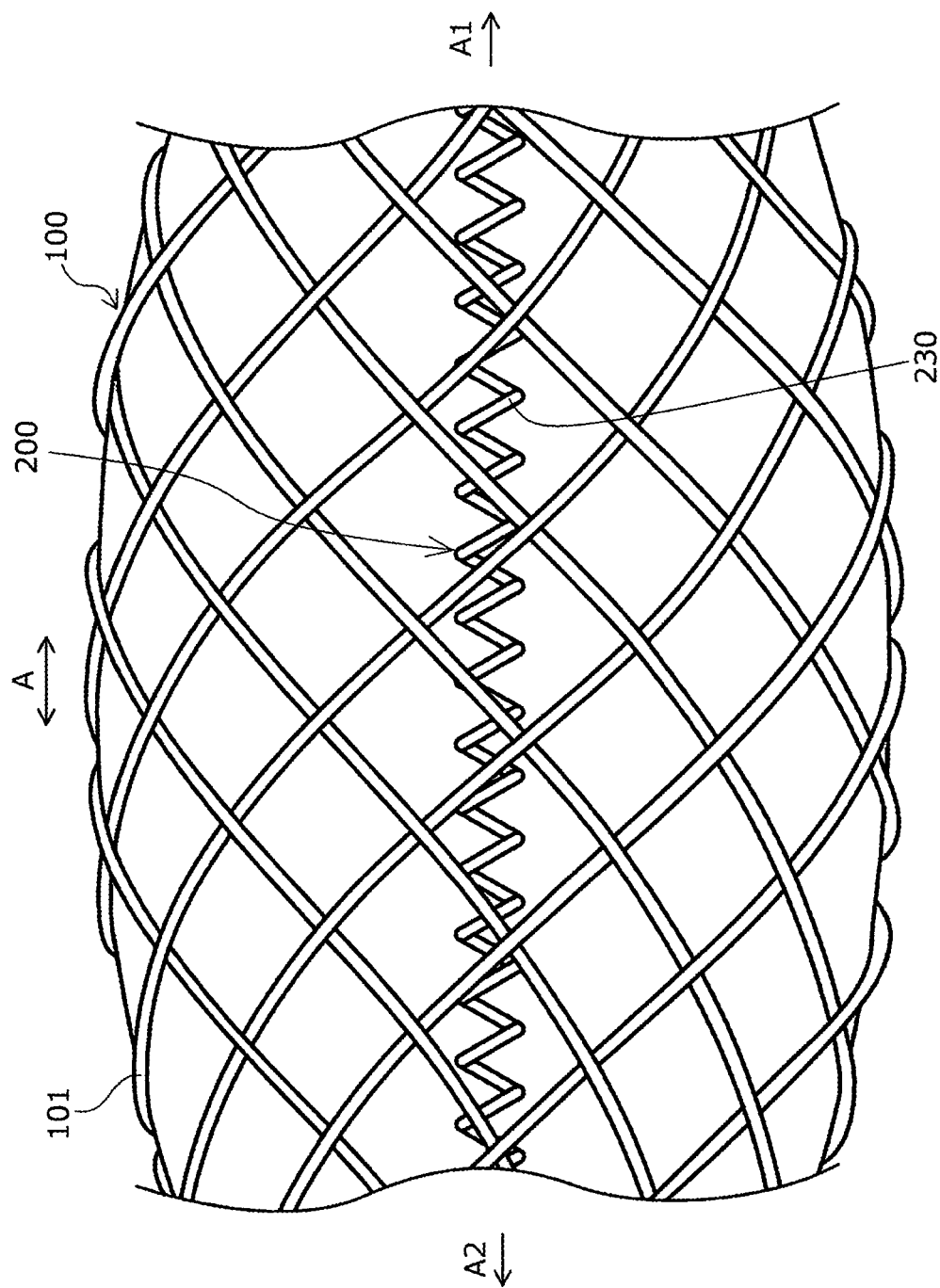
FIG. 5 is a schematic view illustrating a part of the in-tube transit object in FIG. 1 and a state where the in-tube transit object is in the catheter.

In the state where the in-tube transit object 1 is introduced into the catheter 300 as illustrated in FIG. 3, when the in-tube transit object 1 is discharged from a tip 301 of the catheter 300, the first cylindrical section 110 and the second cylindrical section 120 expand in the direction that crosses the longitudinal direction A of the cylindrical body 100, and the coil spring 200 is compressed in the longitudinal direction A of the cylindrical body 100. Here, FIG. 4 illustrates a state where a portion corresponding to the second cylindrical section 120 of the cylindrical body 100 in the in-tube transit object 1 is discharged from the tip 301 of the catheter 300. FIG. 4 illustrates a state where the portion corresponding to the second cylindrical section 120 of the cylindrical body 100 expands in the direction that crosses the longitudinal direction A of the cylindrical body 100 and where the coil spring 200 in the portion corresponding to the second cylindrical section 120 of the cylindrical body 100 is compressed in the longitudinal direction A of the cylindrical body 100. When the entire in-tube transit object 1 is discharged from the tip 301 of the catheter 300, the in-tube transit object 1 is brought into the state illustrated in FIG. 1.

Although not illustrated in the drawings, in the in-tube transit object 1 of this embodiment, a porous layer formed of any of unwoven cloth, a sponge, a film, and a composite body of these is arranged along an inner surface of the cylindrical body 100. Although a material for such a porous layer is not limited, the porous layer is required to have such flexibility that allows a shape change thereof along an inner shape of the cylindrical body 100 in association with an increase or a reduction in the cylindrical diameter of the portion other than the substantially center portion 103 in the cylindrical body 100. However, the present invention is not limited to the in-tube transit object having the porous layer.

In order to facilitate understanding of existence of the coil spring 200 and the interwoven composition of the wiring material 101 in the cylindrical body 100, FIG. 1 to FIG. 5 do not illustrate the wiring material 101 that is arranged on a back side of the sheet. In addition, in order to facilitate understanding of an external shape of the cylindrical body 100, FIG. 1 to FIG. 5 schematically illustrate a part of the external shape of the wiring material 101. Although not limited, in the cylindrical body 100 of this embodiment, in order to set the cylindrical diameter of the substantially center portion 103 to be smaller than the cylindrical diameters of the other portions, the first cylindrical section 110 and the second cylindrical section 120 are woven integrally, and the entire cylindrical body 100 is formed in a sand clock shape, a figure of eight, a double-spindle shape, or a peanut shape.

In the in-tube transit object 1 of this embodiment, except for the coil spring 200, all of the first cylindrical section 110, the second cylindrical section 120, and the porous layer are formed from a bioabsorbable material. Thus, the entire cylindrical body 100 except the coil spring 200 has living body absorbency. Furthermore, treatment for closing the defective hole is performed by changing the shape of the cylindrical body 100. Thus, the cylindrical body 100 is formed of such a material and is formed to have such a woven shape, fiber structure, and fiber cross section that do not damage biological tissues even when the shape of the cylindrical body 100 is changed in the living body.

Normally, the coil spring 200 is formed from a nickel-titanium alloy or the like and does not have the living body absorbency. However, the coil spring 200 may have the living body absorbency by using a magnesium-based alloy. Alternatively, the coil spring 200 may be formed from another metallic alloy, a ternary alloy including three types of metal, or an alloy including four or more types of metal. The coil spring 200 is advantageous in a point that reacts to radiography in the case where the alloy having the living body absorbency is used therefor. Meanwhile, in the case where the alloy that does not have the living body absorbency is used for the coil spring 200, a metallic member does not remain in the body for the entire lifetime. Thus, the coil spring 200 is advantageous in a point that a problem of a defect thereof in a period of distant observation being concerned does not occur.

The wiring material 101 as the bioabsorbable fiber, which constitutes the first cylindrical section 110 and the second cylindrical section 120, is at least one type selected from polyglycolic acid, polylactide (D, L, and DL-forms), polycaprolactone, a glycolate-lactide (D, L, and DL-forms) copolymer, a glycolate-ε-caprolactone copolymer, a lactide (D, L, and DL-forms)-ε-caprolactone copolymer, poly-(p-dioxanone), a glycolate-lactide (D, L, and DL-forms)-ε-caprolactone copolymer, and the like, for example, and is used in the form processed to be monofilament yarn, multifilament yarn, twisted yarn, a braided cord, or the like. However, the wiring material 101 is preferably used in the form of the monofilament yarn.

Furthermore, the material for the wiring material 101 may be a biodegradable alloy. An example of the biodegradable alloy is an alloy based on magnesium as a raw material. For example, a diameter of the wiring material 101 is approximately set to be equal to or larger than 0.001 mm and equal to or smaller than 1.5 mm. An appropriate fiber diameter and an appropriate type are selected for the applied catheterization. In addition, a cross-sectional shape of the wiring material 101 may be any of a circle, an oval, another different shape (for example, a star shape), and the like with a condition of not damaging the biological tissues. Furthermore, a surface of the wiring material 101 may be subjected to hydrophilic treatment by plasma discharge, electron-beam treatment, corona discharge, ultraviolet irradiation, ozone treatment, or the like. Moreover, the wiring material 101 may be subjected to application or impregnation treatment of a radiopaque material (for example, barium sulfate, a gold chip, a platinum chip, or the like), deposit treatment of an agent (for example, the agent suited for the catheterization for the atrial septal defect), or coating treatment using a natural polymer such as collagen or gelatin or a synthetic polymer such as polyvinyl alcohol or polyethylene glycol.

For example, each of the first cylindrical section 110 and the second cylindrical section 120 is produced as braided cord fabric that is made of the wiring material 101 as the monofilament yarn having a desired outer diameter around a silicone rubber tube by using a braiding machine having plural (for example, 8 or 12) yarn feeders, or is formed as a cylindrical body having the substantially same diameter and the interwoven composition by using a circular knitting machine. After the formation, as described above, the first cylindrical section 110 and the second cylindrical section 120 are squeezed in the substantially center portion 103 by a string that is made from the same material as the first cylindrical section 110 and the second cylindrical section 120, and are formed in the sand clock shape, the figure of eight, the double-spindle shape, or the peanut shape including the two cylindrical bodies. Each of the first cylindrical section 110 and the second cylindrical section 120 has a smaller cylindrical diameter than an inner diameter of the catheter when being compressed, and has the cylindrical diameter in preferred size for the catheterization for the atrial septal defect when expanding. For example, the cylindrical diameter of each of the first cylindrical section 110 and the second cylindrical section 120 when being increased is approximately equal to or larger than 5 mm and equal to or smaller than 80 mm and preferably equal to or larger than 15 mm and equal to or smaller than 25 mm. A length of each of the first cylindrical section 110 and the second cylindrical section 120 are provided with such length suitable for the catheterization for the atrial septal defect. Also, a density of the interwoven composition of the cylindrical body 100 is provided with such density suitable for the catheterization for the atrial septal defect. The cylindrical diameters and the lengths of the first cylindrical section 110 and the second cylindrical section 120 do not have to be the same and may be changed to be suitable for the catheterization for the atrial septal defect.

The bioabsorbable material that constitutes the porous layer is not particularly limited. Examples of the bioabsorbable material are synthetic absorbable polymers such as polyglycolic acid, polylactide (D, L, and DL-forms), poly-caprolactone, the glycolate-lactide (D, L, and DL-forms) copolymer, a glycolate-ε-caprolactone copolymer, the lactide (D, L, and DL-forms)-ε-caprolactone copolymer, poly-(p-dioxanone), and the glycolate-lactide (D, L, and DL-forms)-ε-caprolactone copolymer. These polymers may be used alone, or two or more types thereof may be used concurrently. Of these, at least one type selected from a group including polyglycolic acid, the lactide (D, L, and DL-forms)-ε-caprolactone copolymer, the glycolate-ε-caprolactone copolymer, and the glycolate-lactide (D, L, and DL-forms)-ε-caprolactone copolymer is preferred due to exhibition of appropriate degradation behavior. The porous layer is formed of any of the unwoven cloth, the sponge, the film, and the composite body of these. In particular, as a preferred aspect, the unwoven cloth can be exemplified.

Furthermore, a material for the porous layer may be the biodegradable alloy. An example of such a biodegradable alloy is the alloy based on magnesium as the raw material. In the case where the porous layer is formed of the unwoven cloth, the porous layer may be subjected to the hydrophilic treatment. The hydrophilic treatment is not particularly limited, and examples of the hydrophilic treatment are plasma treatment, glow discharge treatment, corona discharge treatment, the ozone treatment, surface graft treatment, and ultraviolet irradiation treatment. Of these, the plasma treatment is preferred since a water absorption rate can dramatically be improved without changing external appearance of the unwoven cloth layer. The porous layer may be a sponge layer or a film layer, or may be a composite layer of the unwoven cloth and the sponge layer, a composite layer of the unwoven cloth and the film layer, a composite layer of the sponge layer and the film layer, or a composite layer of the unwoven cloth, the sponge layer, and the film layer. It is also preferred that the agent suited for the catheterization for the atrial septal defect is kept in the porous layer.

(Usage of In-Tube Transit Object)

A description will hereinafter be made on a case where the in-tube transit object 1 of this embodiment is used for the catheterization for the atrial septal defect with reference to FIG. 6 to FIG. 9. The following description will only be made on matters unique to usage of the in-tube transit object 1 of this embodiment. Meanwhile, a description on general matters will be the same as that on the catheterization for the known atrial septal defect. Thus, a detailed description thereon will not be made.

Figure 6:
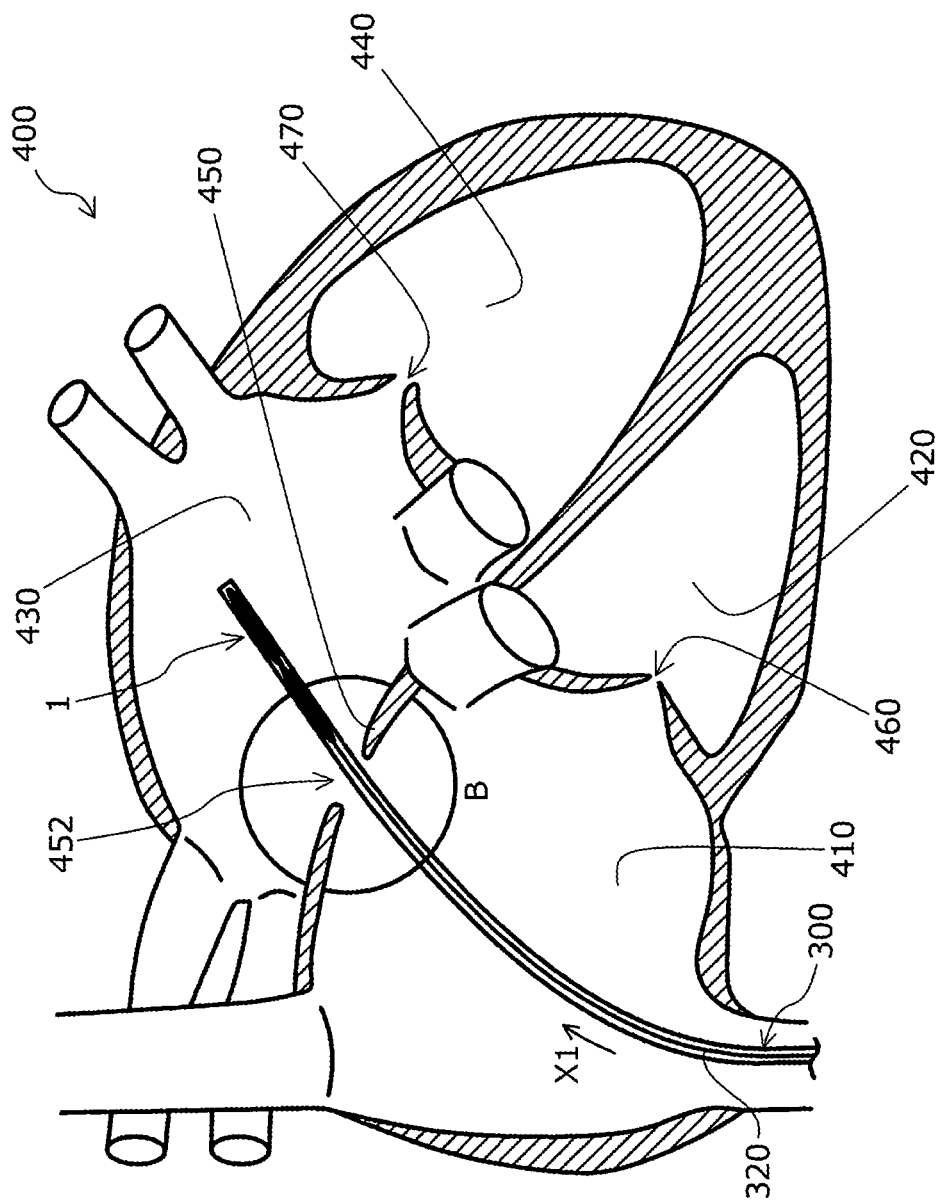
FIG. 6 is a conceptual view of a case where the in-tube transit object in FIG. 1 is used for catheterization for an atrial septal defect.

As illustrated in FIG. 6, a human heart 400 is configured to include two atria and two ventricles that are: a right atrium 410 that is connected to a superior vena cava and an inferior vena cava and receives venous blood from a whole body; a right ventricle 420 that is connected to the right atrium 410 via a pulmonary artery and a tricuspid valve 460 and pumps out the venous blood to a lung; a left atrium 430 that is connected to a pulmonary vein and receives arterial blood from the lung; and a left ventricle 440 that is connected to an aorta and a mitral valve 470 and pumps out the arterial blood to the entire body. The atrial septal defect is a disease that a defective hole 452 is opened in an atrial septal 450 that divides the right atrium 410 and the left atrium 430.

First, on the outside of the living body, the end on the direction A1 side and the end on the direction A2 side of the in-tube transit object 1 having the first cylindrical section 110 and the second cylindrical section 120, each of which expands to appropriate size for the defective hole 452, are pulled in a separating direction, the entire coil spring 200 is thereby extended to reduce the cylindrical diameter of the cylindrical body 100 (the outer diameters of the first cylindrical section 110 and the second cylindrical section 120) having the porous layer to be smaller than the inner diameter of the catheter 300. Then, the in-tube transit object 1 is set in the catheter 300. The catheter 300 that accommodates the in-tube transit object 1 is inserted from a femoral vein, the catheter 300 is then moved to an arrow X1 direction through the defective hole 452 from the right atrium 410 side, and the catheter 300 that accommodates the in-tube transit object 1 is brought closer to the left atrium 430 side.

Figure 7:
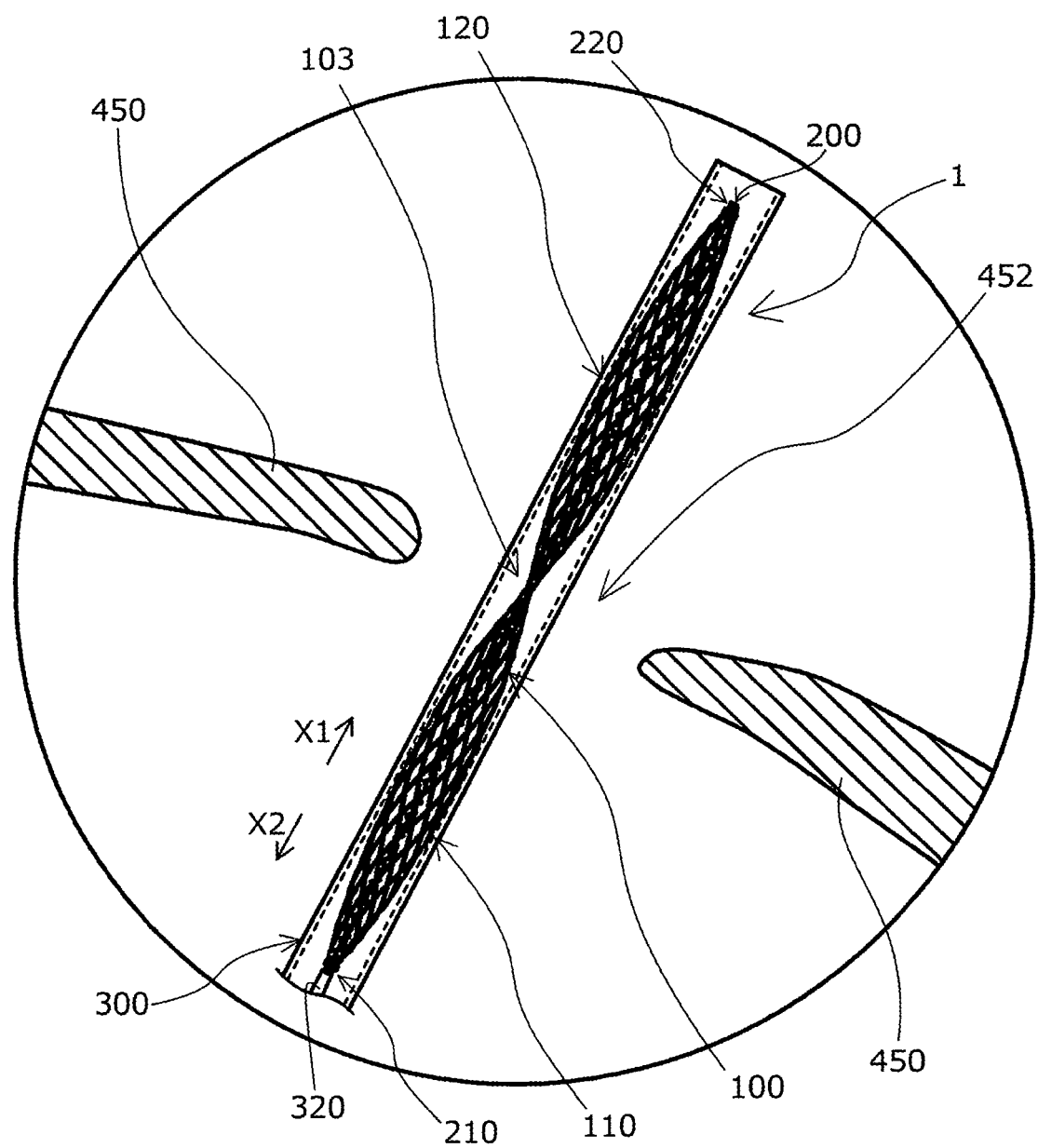
FIG. 7 is a view illustrating a procedure of the catheterization using the in-tube transit object in FIG. 1, and is a schematic view of an area B in FIG. 6 that corresponds to the state illustrated in FIG. 3 and illustrates the state where the in-tube transit object in FIG. 1 is in the catheter.
Figure 8:
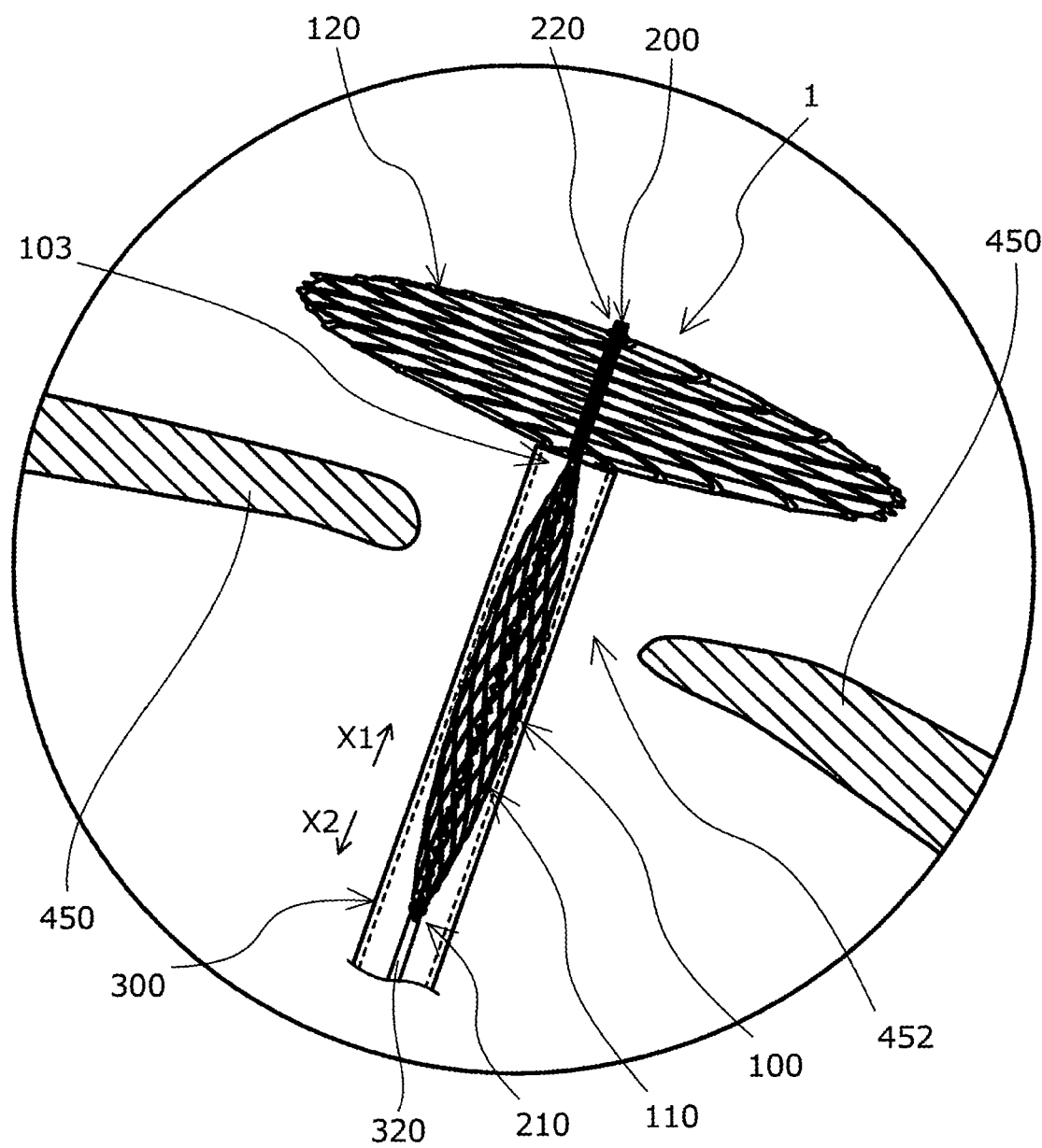
FIG. 8 is a view illustrating the procedure of the catheterization using the in-tube transit object in FIG. 1, and is a schematic view of the area B in FIG. 6 that corresponds to the state illustrated in FIG. 4 and illustrates a state where the in-tube transit object in FIG. 1 is partially discharged from the catheter.

As illustrated in FIG. 6 and FIG. 7, the catheter 300 that accommodates the in-tube transit object 1 is stopped at a position at which the substantially center portion 103 of the cylindrical body 100 is located near the defective hole 452. In the living body, when a wire 320 pushes out the second cylindrical section 120 from the catheter 300 in the arrow X1 direction, the second cylindrical section 120, the shape of which has been restricted by an inner wall 310 of the catheter 300, can freely change the shape. As a result, only a portion of the coil spring 200 that is included in the second cylindrical section 120 is compressed, and only the second cylindrical section 120 and the porous layer corresponding to a position of the second cylindrical section 120 expand as illustrated in FIG. 8.

Then, when the wire 320 further pushes out the first cylindrical section 110 from the catheter 300 in the arrow X1 direction, the first cylindrical section 110, the shape of which has been restricted by the inner wall 310 of the catheter 300, can also freely change the shape. As a result, a portion of the coil spring 200 that is included in the first cylindrical section 110 is also compressed, and the first cylindrical section 110 and the porous layer corresponding to a position of the first cylindrical section 110 expand as illustrated in FIG. 9.

That is, when the wire 320 pushes out the in-tube transit object 1 from the catheter 300, the second cylindrical section 120, which is arranged on the left atrium side, and the porous layer, which corresponds to the position of the second cylindrical section 120, first expand. Then, the first cylindrical section 110, which is arranged on the right atrium side, and the porous layer, which corresponds to the position of the first cylindrical section 110, expand later. As a result, a pair of the first cylindrical section 110, which is arranged on the right atrium side, and the porous layer, which corresponds to the position of the first cylindrical section 110, and a pair of the second cylindrical section 120, which is arranged on the left atrium side, and the porous layer, which corresponds to the position of the second cylindrical section 120, approach each other with the substantially center portion 103 being the reference. In addition, the first cylindrical section 110, the porous layer corresponding to the position of the first cylindrical section 110, the second cylindrical section 120, and the porous layer corresponding to the position of the second cylindrical section 120 expand. In the end, the atrial septal 450 is held from both sides by the pair of the first cylindrical section 110 and the porous layer corresponding to the position of the first cylindrical section 110 and the pair of the second cylindrical section 120 and the porous layer corresponding to the position of the second cylindrical section 120. Then, as illustrated in FIG. 9, the in-tube transit object 1 can close the defective hole 452 that is opened to the atrial septal 450. When the in-tube transit object 1 is discharged from the catheter 300, the catheter 300 may be moved to the arrow X1 direction and an arrow X2 direction (that is, position adjustment) so as to adjust a discharge position of the in-tube transit object 1 in the arrow X1 direction and the arrow X2 direction with respect to the defective hole 452.

Thereafter, the wire 320 and the catheter 300 are moved in the arrow X2 direction, the wire 320 and the catheter 300 are taken out of the living body, and the treatment is thereby completed. The wire 320 may be taken out of the living body in association with taking the catheter 300 out of the living body. However, the wire 320 may be taken out of the living body prior to the catheter 300. In a process as described above, the in-tube transit object 1, almost all of which is formed from the bioabsorbable material except for the coil spring 200, remains in the living body. Since almost all of the material for the in-tube transit object 1, which remains in the living body, is the bioabsorbable material, the in-tube transit object 1 is absorbed into the living body in the end. Therefore, there is hardly a possibility of a defect in a period of distant observation.

Figure 9:
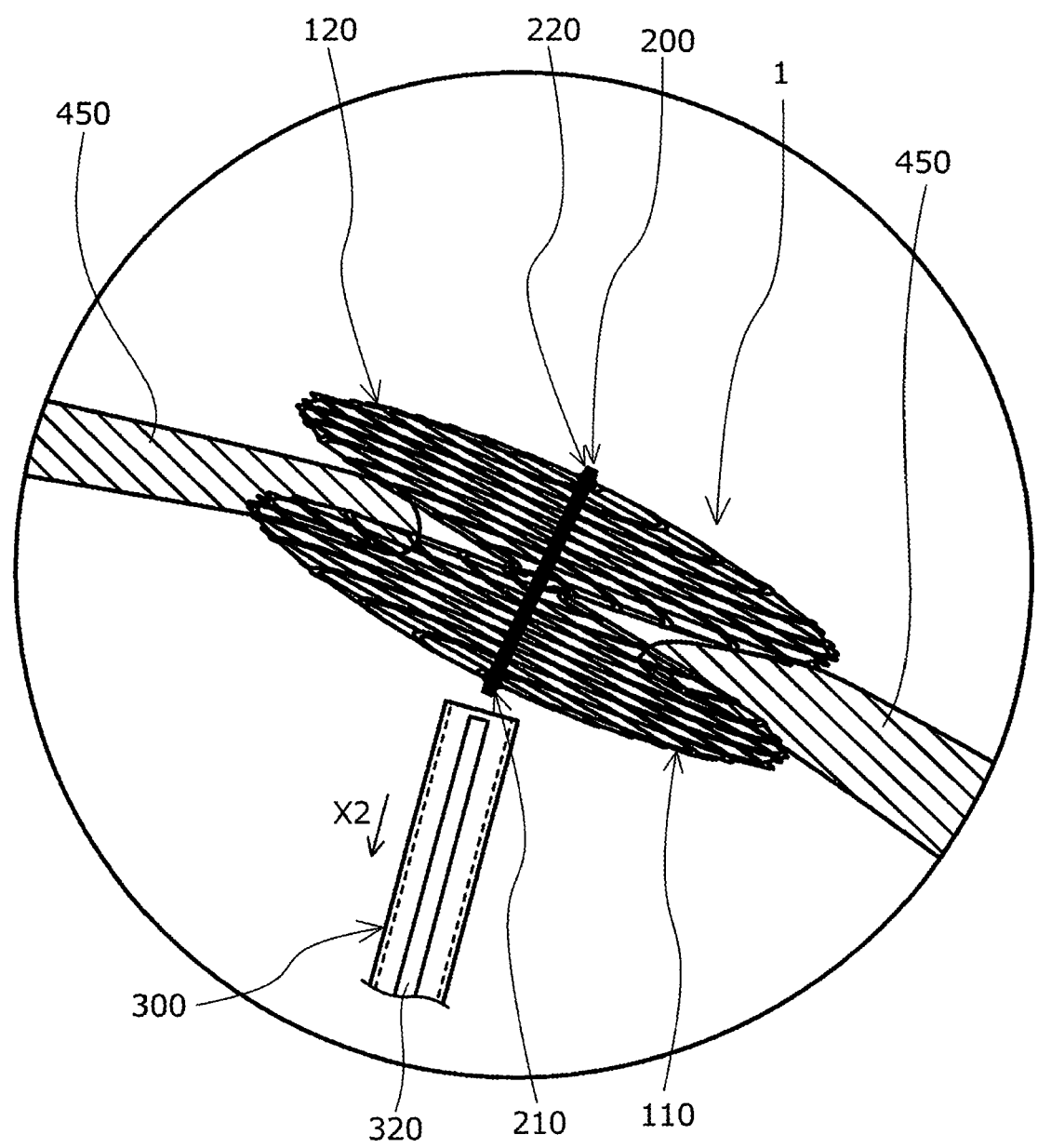
FIG. 9 is a view illustrating the procedure of the catheterization using the in-tube transit object in FIG. 1, and is a schematic view of the area B in FIG. 6 that illustrates a state where the entire in-tube transit object in FIG. 1 is discharged from the catheter and detached from a wire.

In the case where the in-tube transit object 1 that does not include the coil spring 200 is used, it is necessary to fix the shape of the cylindrical body 100 to the shape illustrated in FIG. 9 before the in-tube transit object 1 is placed in in the living body. For example, it has been considered to provide the wiring material 101 with thermal adhesiveness and thermally set the wiring material 101 in the living body. However, in the in-tube transit object 1 having the configuration as in this embodiment, the shape of the cylindrical body 100 can be fixed to the shape illustrated in FIG. 9 by the coil spring 200. Therefore, the in-tube transit object 1 is advantageous.

As it has been described so far, almost all of the in-tube transit object 1 according to this embodiment is formed from the bioabsorbable material, and is absorbed into the body in the end. Therefore, there is hardly the possibility of the defect in the period of distant observation. In addition, due to the provision of the coil spring 200, the cylindrical diameter of the cylindrical body 100 is easily changed with the porous layer. Thus, the cylindrical body 100 can easily be set in the catheter 300 by finely changing the cylindrical diameter of the cylindrical body 100 and the size of the porous layer. Furthermore, due to the provision of the coil spring 200, which causes the cylindrical body 100 to expand simply by pushing out the in-tube transit object 1 from the catheter 300, at the position of the defective hole 452, the cylindrical diameter of the cylindrical body 100 can easily be increased with the porous layer so as to make the two cylindrical bodies (the first cylindrical section 110 and the second cylindrical section 120) approach each other. Moreover, since the shape of the cylindrical body 100 can easily be fixed, it is possible to easily close the defective hole 452 that is opened to the atrial septal.

(Detailed Configuration of Coil Spring)

A description will hereinafter be made on a detailed configuration of the coil spring 200 in this embodiment. As described above, the coil spring 200 has the large diameter sections 201, in each of which a winding diameter of the element wire 230 is larger in one direction than the winding diameters of the other portions, at the end 210 on the direction A1 side and at the end 220 on the direction A2 side (see FIG. 10 and FIG. 11). As illustrated in FIG. 11, the coil spring 200 of this embodiment includes, as the large diameter sections 201, two each of: a first large diameter section 201A, a winding diameter of which is large on a first direction side (an upper side in FIG. 11) when seen from the direction A1 side; a second large diameter section 201B, a winding diameter of which is large on a second direction side (a lower side in FIG. 11) when seen from the direction A1 side; a third large diameter section 201C, a winding diameter of which is large on a third direction side (a left side in FIG. 11) when seen from the direction A1 side; and a fourth large diameter section 201D, a winding diameter of which is large on a fourth direction side (a right side in FIG. 11) when seen from the direction A1 side.

The first cylindrical section 110 is attached to the coil spring 200 when the wiring material 101 at the end on the direction A1 side of the first cylindrical section 110 in the cylindrical body 100 is inserted through the hole sections 202 at two each positions in the first large diameter section 201A, the second large diameter section 201B, the third large diameter section 201C, and the fourth large diameter section 201D formed on the direction A1 side, that is, at a total of eight positions calculated by multiplying the four directions by the two positions. Similarly, the second cylindrical section 120 is attached to the coil spring 200 when the wiring material 101 at the end on the direction A2 side of the second cylindrical section 120 in the cylindrical body 100 is inserted through the hole sections 202 at two each positions in the first large diameter section 201A, the second large diameter section 201B, the third large diameter section 201C, and the fourth large diameter section 201D formed on the direction A2 side, that is, at a total of eight positions. In FIG. 11, the positions through each of which the wiring material 101 is inserted are indicated by broken lines. In this embodiment, as illustrated in FIG. 11, the two wiring materials 101 are inserted through each of the hole sections 202. However, the number of the wiring material 101 inserted through the hole section 202 is not particularly limited.

Figure 12:
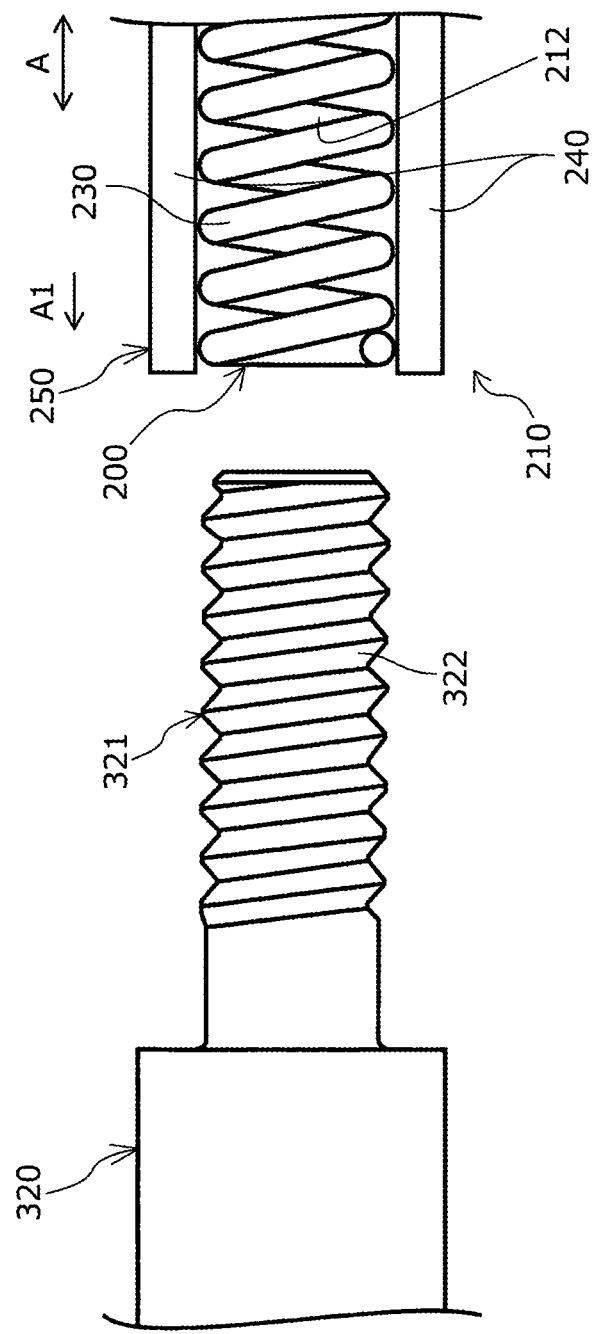
FIG. 12 is a schematic view illustrating an attachment/detachment section of the coil spring in the in-tube transit object in FIG. 1, the attachment/detachment section being attached/detached to/from the wire.

Next, a description will be made on an attachment/detachment section 250 of the coil spring 200 to/from the wire 320 with reference to FIG. 12. As illustrated in FIG. 12, the wire 320 of this embodiment has a tip portion 321 having a male screw 322 and is configured to be able to rotate the tip portion 321 with the longitudinal direction A of the cylindrical body 100 being a rotational axis. In addition, as illustrated in FIG. 12, the end 210 on the direction A1 side of the attachment/detachment section 250 is formed with a female screw 212, which corresponds to the male screw 322, by the element wire 230 for forming the coil spring 200. Furthermore, the cylindrical pipe 240 is fitted to the end 210 such that the female screw 212 formed of the element wire 230 does not expand radially.

Since the attachment/detachment section 250 of the coil spring 200 to/from the wire 320 is configured just as described, the in-tube transit object 1 of this embodiment can easily be attached/detached to/from the wire 320 by rotating the tip portion 321 of the wire 320. For example, when the catheter 300 is introduced up to a desired position and the tip portion 321 of the wire 320 is rotated at the desired position, the in-tube transit object 1 can easily be arranged at an accurate position.

Here, the in-tube transit object 1 of this embodiment will be summarized. The in-tube transit object 1 of this embodiment is the in-tube transit object that is inserted through the catheter 300 (the inner wall 310) as the inside of the tube, and includes: the coil spring 200 as the coil section that is formed by winding the element wire 230; and the cylindrical body 100 as the fiber section that is attached to the end 210 on the one side and the end 220 on the other side in the winding-axis direction of the coil spring 200 (a direction along the longitudinal direction A of the cylindrical body 100). The coil spring 200 is formed with the large diameter sections 201 as hole formed sections, through each of which the wiring material 101 as the fiber of the cylindrical body 100 is inserted, at the end 210 on the one side and the end 220 on the other side. When the in-tube transit object 1 is inserted in the catheter 300, the coil spring 200 is also inserted in an extending state in the winding-axis direction. In addition, the cylindrical body 100 is configured to expand when seen in the winding-axis direction in the case where the in-tube transit object 1 is inserted in the catheter 300, is then discharged from the catheter 300, and the coil spring 200 is thereby brought into the compressed state in the winding-axis direction.

As described above, the in-tube transit object 1 of this embodiment is formed with the large diameter sections 201, through each of which the wiring material 101 is inserted, at the end 210 on the one side and the end 220 on the other side in the winding-axis direction of the coil spring 200. Accordingly, the large diameter section 201 as a portion to which the wiring material 101 is attached can be formed by a simple method for increasing the winding diameter of the element wire 230. In addition, the attachment position of the wiring material 101 is suppressed from being displaced by inserting the wiring material 101 through the large diameter section 201. Thus, the in-tube transit object 1 of this embodiment is easily provided with such a configuration that the cylindrical body 100 expands in association with the discharge of the in-tube transit object 1 from the catheter 300 after the insertion of the in-tube transit object 1 in the catheter 300.

The hole formed section in the in-tube transit object 1 of this embodiment is the large diameter section 201 that is formed by increasing the winding diameter of the element wire 230 to be larger than the winding diameters of the other portions in the coil spring 200. However, the present invention is not limited to the hole formed section with such a configuration. It may be configured that a cut component or the like formed with a hole through which the wiring material 101 is inserted, is attached to the coil spring 200. In a case of such a configuration, "the coil section that is formed by winding the element wire 230" includes a configuration that another component is attached to a single coil body. The method for attaching another component to the coil spring 200 is not particularly limited. Any of various methods such as welding and caulking can be used.

In addition, as described above, the cylindrical body 100 of this embodiment is configured to expand at the two positions of the end 210 on the one side (that is, the first cylindrical section 110) and the end 220 on the other side (that is, the second cylindrical section 120) when seen in the winding-axis direction in the case where the in-tube transit object 1 is inserted in the catheter 300, is then discharged from the catheter 300, and the coil spring 200 is thereby brought into the compressed state in the winding-axis direction. Accordingly, for example, as illustrated in FIG. 9, when being discharged from the catheter 300, the cylindrical body 100 is arranged to hold the defective hole 452 at the two positions, and can thereby close the defective hole 452. However, in this embodiment, the in-tube transit object 1 has such a configuration since the in-tube transit object 1 serves as the defective hole closing member that can be used for the catheterization for the patient having the atrial septal defect. Thus, the in-tube transit object 1 is not limited to have such a configuration in the case where the in-tube transit object 1 is used for another application or the like.

As described above, at each of the end 210 and the end 220, the coil spring 200 of this embodiment has the four large diameter sections 201 when seen in the longitudinal direction A of the cylindrical body 100, and the four large diameter sections 201 are the first large diameter section 201A, the second large diameter section 201B, the third large diameter section 201C, and the fourth large diameter section 201D. In other words, in the in-tube transit object 1 of this embodiment, the coil spring 200 is formed with the large diameter sections 201 so as to form the hole sections 202, through each of which the wiring material 101 is inserted, at plural positions (in the four directions) when the coil spring 200 is seen in the winding-axis direction. Thus, compared to a configuration that the hole section 202, through which the wiring material 101 is inserted, is only formed at one position, the configuration of the in-tube transit object 1 in this embodiment allows further reliable attachment of the cylindrical body 100 to the coil spring 200.

As described above, each of the large diameter sections 201 in this embodiment is formed by increasing the winding diameter of the element wire 230 in the one direction to be larger than the winding diameters of the other portions. In addition, as illustrated in FIG. 10, two each of the first large diameter sections 201A, the second large diameter sections 201B, the third large diameter sections 201C, and the fourth large diameter sections 201D are provided at both of the end 210 and the end 220. In other words, when the coil spring 200 of this embodiment is seen in the winding-axis direction, the coil spring 200 is formed such that the first large diameter sections 201A, the second large diameter sections 201B, the third large diameter sections 201C, and the fourth large diameter sections 201D as the plural large diameter sections 201 overlap each other. Accordingly, in the coil spring 200 of this embodiment, the single wiring material 101 can be inserted in each of the hole sections 202 of the plural large diameter sections 201. Therefore, it is possible to increase strength of portions, through which of which the wiring material 101 is inserted. Here, it is needless to say that a meaning of "overlap" includes a configuration that the adjacent element wires 230 overlap each other. In addition, the meaning of "overlap" also includes a configuration that the element wires 230 not adjacent to each other overlap as in this embodiment.

The coil spring 200 of this embodiment is made from the nickel-titanium alloy. The coil spring 200 is preferably made of metal. This is because the coil spring 200 can have high strength. In addition, the coil spring 200 is particularly preferably made from an alloy of nickel and titanium. The alloy of nickel and titanium is especially superior in biological compatibility, and thus can particularly favorably be used in the medical field and the like, for example.

Here, the in-tube transit object 1 of this embodiment is the in-tube transit object that is inserted in the catheter 300 as the tube. However, the in-tube transit object of the present invention may have a configuration of being inserted in a tube other than the catheter. When the configuration as that of the in-tube transit object 1 in this embodiment is adopted, it is possible to be easily configured that the fiber section expands in association with the discharge of the in-tube transit object from the tube after the insertion of the in-tube transit object in the tube. Thus, the configuration as that of the in-tube transit object 1 in this embodiment can favorably be adopted as the configuration of the in-tube transit object for the catheter.

As described above, the coil spring 200 in this embodiment has the attachment/detachment section 250 to/from the wire 320 that is inserted in the catheter 300. The wire 320 has the rotatable male screw 322 in the tip portion 321. Here, as the attachment/detachment section 250, the female screw 212 that corresponds to the male screw 322 is provided an inner side of the coil spring 200. Just as described, when the female screw 212 is formed as the attachment/detachment section 250 on the inner side of the coil spring 200, the attachment/detachment section 250 can easily be formed. Here, "has(having) the rotatable male screw 322 in the tip portion 321" means not only a configuration that only the male screw 322 of the tip portion 321 rotates with respect to the wire 320 and also a configuration that the male screw 322 of the tip portion 321 also rotates by rotating the entire or partial wire 320. However, the present invention is not limited to such a configuration. It is also possible to cut the coil spring 200 from the wire 320 by a cutting device such as a cutter or by heating the coil spring 200.

As described above, the attachment/detachment section 250 of this embodiment has the pipe 240 as a tubular section that covers an outer circumference of the female screw 212. Since the attachment/detachment section 250 has the pipe 240 that covers the outer circumference of the female screw 212, it is possible to suppress the coil spring 200 from expanding radially. In the case where the male screw 322 is inserted in the attachment/detachment section 250 of the coil spring 200, and the coil spring 200 thereby expands radially, meshing between the male screw 322 and the female screw 212 becomes defective, which possibly prevents the female screw 212 of the attachment/detachment section 250 from playing a role as the female screw 212. However, when the outer circumference of the female screw 212 is covered with the pipe 240, such a problem can be suppressed.

Figure 13:
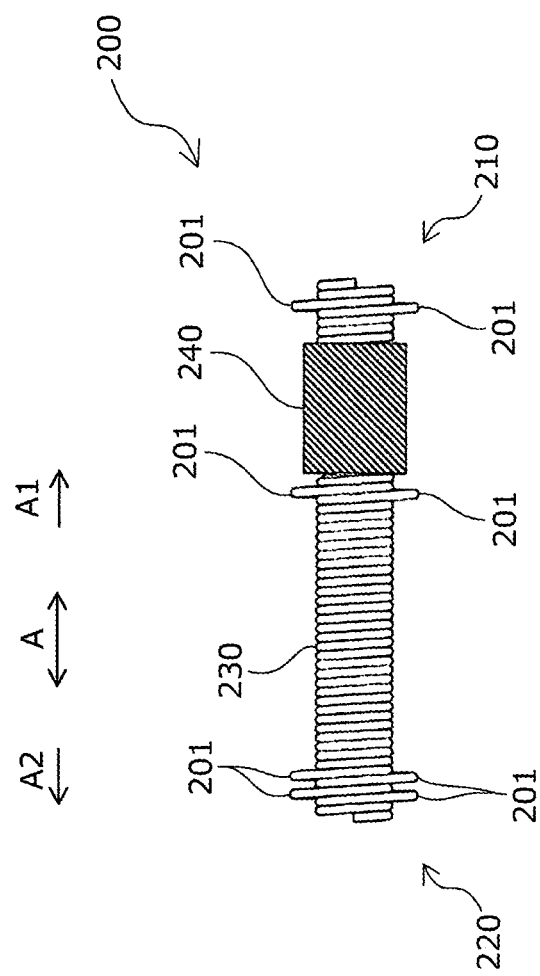
FIG. 13 is a schematic view illustrating a coil spring of an in-tube transit object according to a second embodiment of the present invention.
Figure 14:
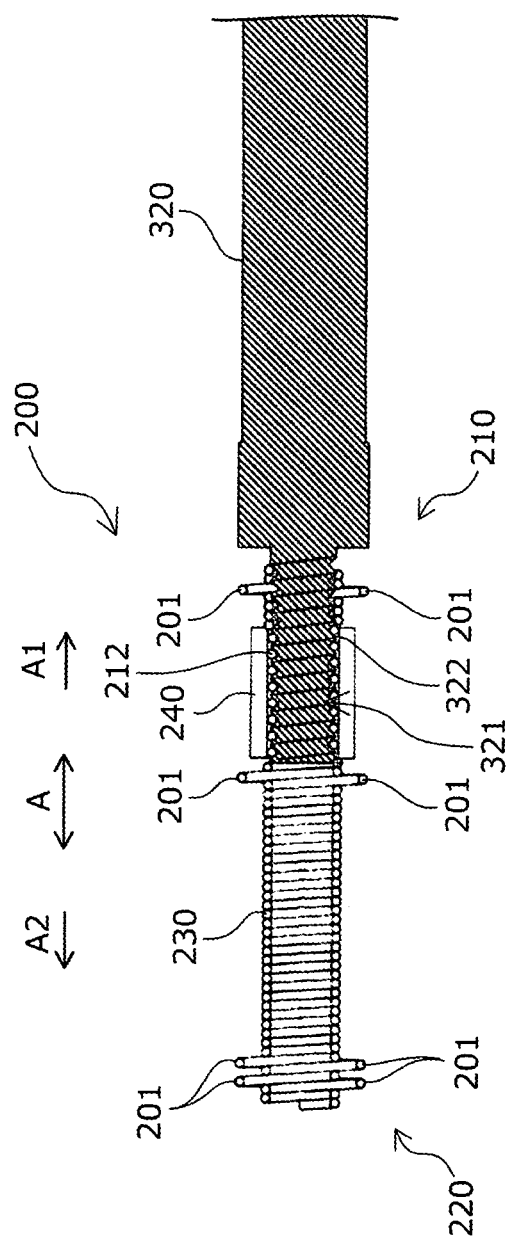
FIG. 14 is a schematic cross-sectional view illustrating a state where a wire is attached to the coil spring of the in-tube transit object according to the second embodiment of the present invention.
Figure 15:
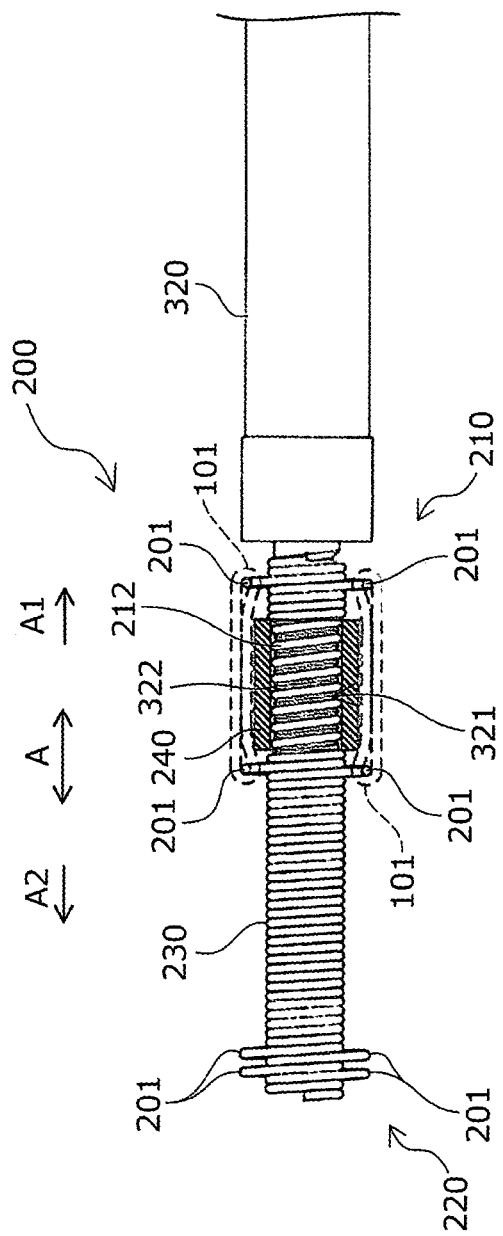
FIG. 15 is a schematic cross-sectional view illustrating the state where the wire is attached to the coil spring of the in-tube transit object according to the second embodiment of the present invention and a state where the in-tube transit object is inserted in a catheter.

[Second Embodiment] (FIG. 13 to FIG. 15)

Next, a description will be made on an in-tube transit object 1 according to a second embodiment with reference to FIG. 13 to FIG. 15. In FIG. 13 to FIG. 15, common components to those in the above first embodiment will be denoted by the same reference numerals, and the detailed description thereon will not be made. Here, the in-tube transit object 1 of this embodiment has similar characteristics to the in-tube transit object 1 of the first embodiment described above, and has a similar shape to the in-tube transit object 1 of the first embodiment except for portions, which will be described below.

As illustrated in FIG. 13 to FIG. 15, in the coil spring 200 of the in-tube transit object 1 in this embodiment, the pipe 240 is provided at a position between the plural large diameter sections 201 that are formed on the end 210 side. As illustrated in FIG. 14 and FIG. 15, the pipe 240 suppresses the female screw 212 of the coil spring 200 from being pushed by the male screw 322 in the tip portion 321 of the wire 320 and expanding in a direction that crosses the longitudinal direction A in the case where the tip portion 321 of the wire 320 is inserted from the end 210 side of the coil spring 200.

Here, as illustrated in FIG. 15, when the in-tube transit object 1, which is attached to the wire 320, is inserted in the catheter 300, the large diameter sections 201 on both sides of the pipe 240 are connected by a part of the wiring material 101 that is indicated by broken lines. Just as described, since the large diameter sections 201 on both of the sides of the pipe 240 are rigidly connected by the part of the wiring material 101, the coil spring 200 can endure a tensile force during the insertion in the catheter 300. In other words, the coil spring 200 is suppressed from extending along the longitudinal direction A due to the tensile force during the insertion in the catheter 300.

Figure 16:
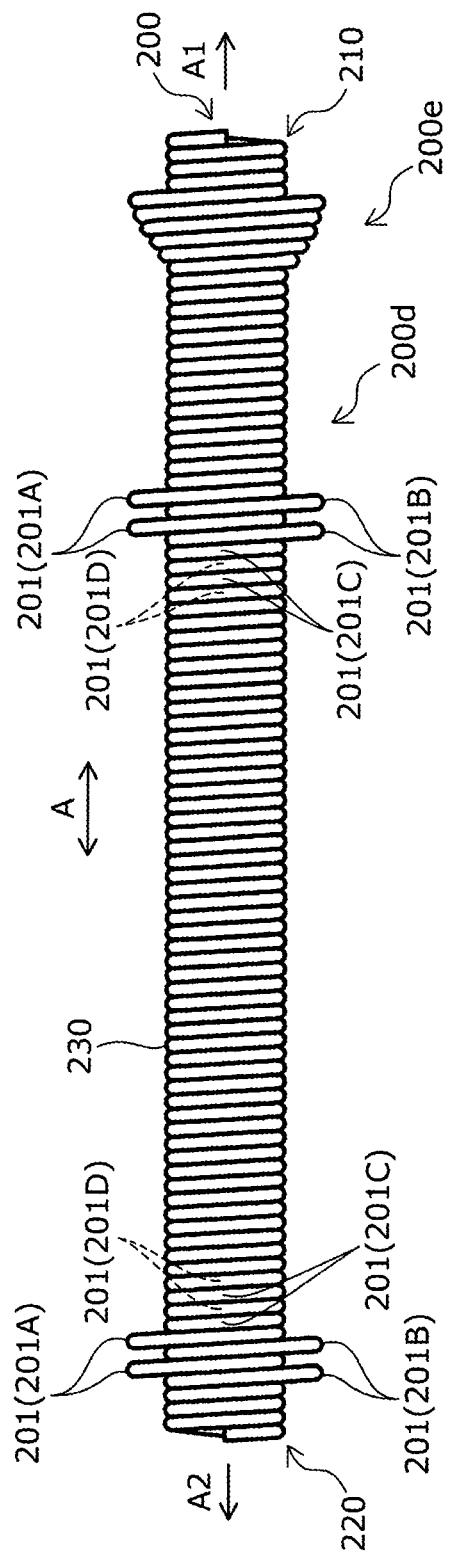
FIG. 16 is a schematic view in which a coil spring of an in-tube transit object according to a third embodiment of the present invention is seen from a direction that crosses a winding-axis direction.
Figure 17:
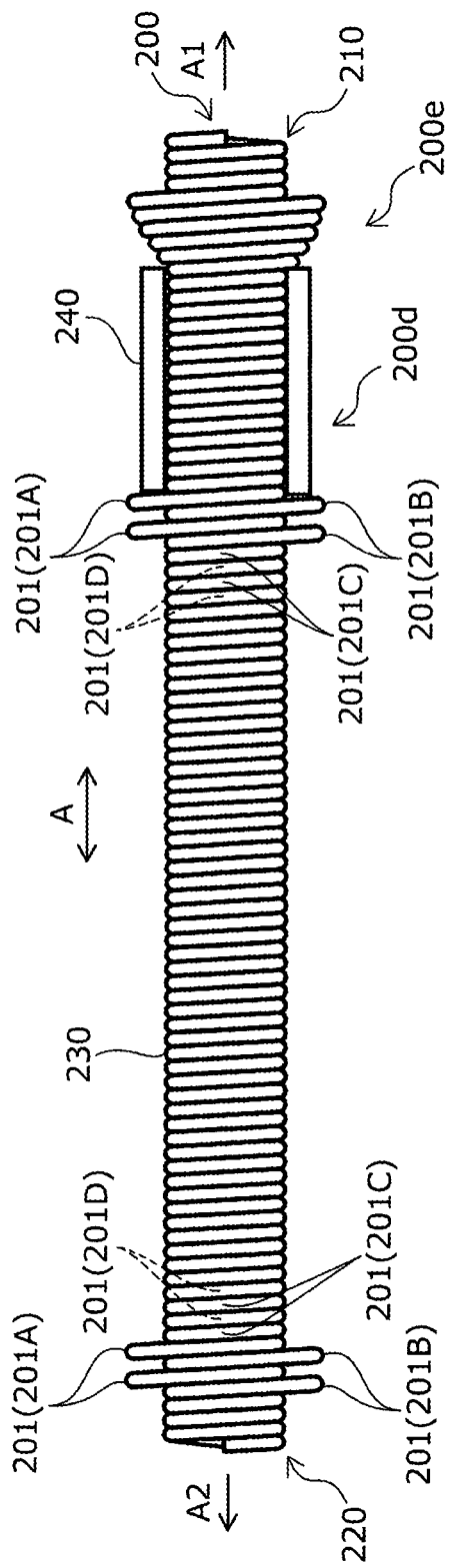
FIG. 17 is a schematic view in which the coil spring of the in-tube transit object according to the third embodiment of the present invention is seen from the direction that crosses the winding-axis direction, and is a view illustrating a state where a pipe is fitted to the coil spring.

[Third Embodiment] (FIG. 16 and FIG. 17)

Next, a description will be made on an in-tube transit object 1 according to a third embodiment with reference to FIG. 16 and FIG. 17. In FIG. 16 and FIG. 17, common components to those in the above first embodiment and second embodiment will be denoted by the same reference numerals, and the detailed description thereon will not be made. Here, the in-tube transit object 1 of this embodiment has similar characteristics to the in-tube transit objects 1 of the first embodiment and the second embodiment described above, and has a similar shape to the in-tube transit objects 1 of the first embodiment and the second embodiment except for portions, which will be described below.

As illustrated in FIG. 16 and FIG. 17, the coil spring 200 of the in-tube transit object 1 in this embodiment is formed with an extended coil section 200d and an end-side large diameter section 200e, a coil diameter of which is gradually increased outward, on an outer side of the large diameter section 201 on the end 210 side. As illustrated in FIG. 17, the pipe 240 is fitted to the extended coil section 200d and is positioned by the large diameter section 201 and the end-side large diameter section 200e. The male screw 322 of the wire 320 is threaded to the inside of the extended coil section 200d as the female screw 212. Like the in-tube transit object 1 of this embodiment, it may be configured that the pipe 240 is fitted to the outer side of the large diameter section 201.

Figure 18:
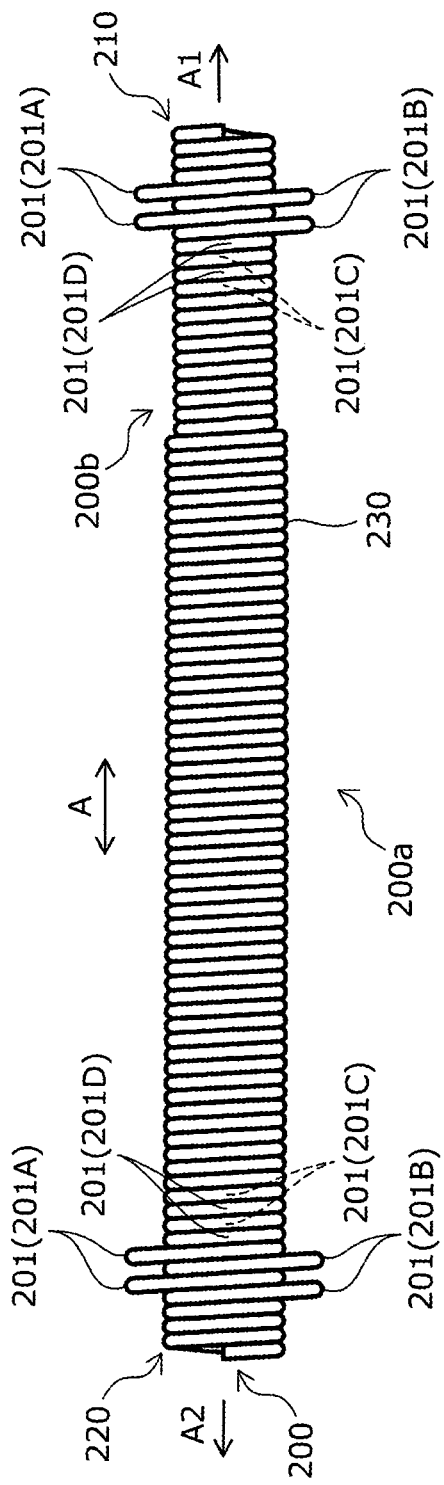
FIG. 18 is a schematic view in which a coil spring of an in-tube transit object according to a fourth embodiment of the present invention is seen from a direction that crosses a winding-axis direction.
Figure 19:
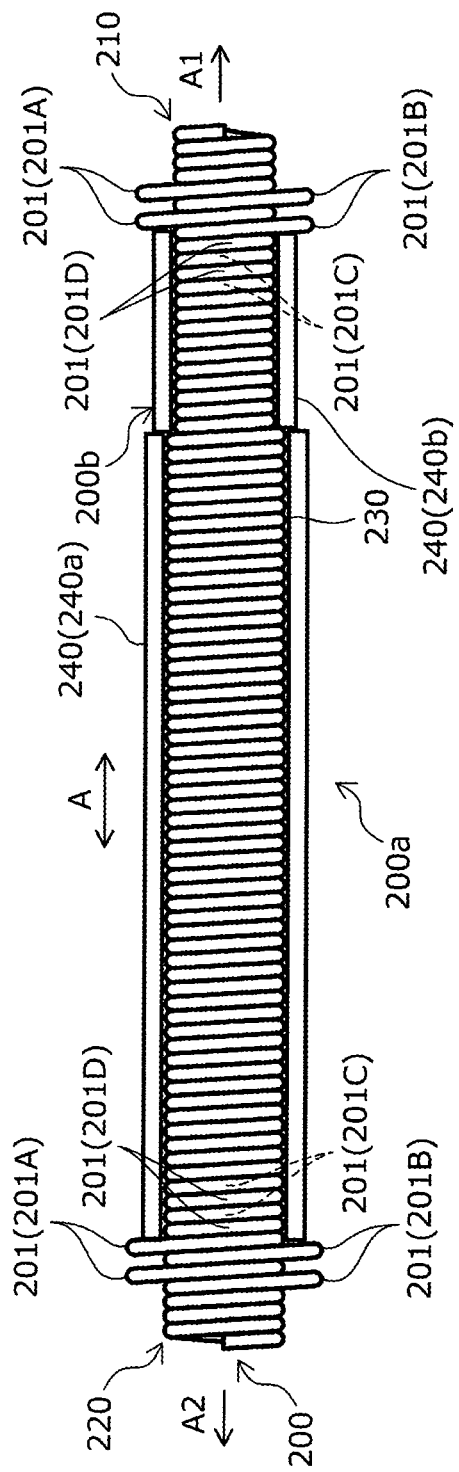
FIG. 19 is a schematic view in which the coil spring of the in-tube transit object according to the fourth embodiment of the present invention is seen from the direction that crosses the winding-axis direction, and is a view illustrating a state where a pipe is fitted to the coil spring.

[Fourth Embodiment] (FIG. 18 and FIG. 19)

Next, a description will be made on an in-tube transit object 1 according to a fourth embodiment with reference to FIG. 18 and FIG. 19. In FIG. 18 and FIG. 19, common components to those in the above first embodiment to third embodiment will be denoted by the same reference numerals, and the detailed description thereon will not be made. Here, the in-tube transit object 1 of this embodiment has similar characteristics to the in-tube transit objects 1 of the first embodiment to the third embodiment described above, and has a similar shape to the in-tube transit objects 1 of the first embodiment to the third embodiment except for portions, which will be described below.

As illustrated in FIG. 18 and FIG. 19, the coil spring 200 of the in-tube transit object 1 in this embodiment is formed with a first area 200a with a large coil diameter and a second area 200b, a coil diameter of which is smaller than that of the first area 200a, between the large diameter section 201 on the end 210 side and the large diameter section 201 on the end 220 side. The male screw 322 of the wire 320 is threaded to the inside of the second area 200b as the female screw 212. Like the in-tube transit object 1 of this embodiment, the coil spring 200 may be configured that the areas with different coil diameters are provided and that the wire 320 is fitted to the inside of one of the areas.

In addition, as illustrated in FIG. 19, the coil spring 200 of the in-tube transit object 1 in this embodiment has, as the pipe 240: a first pipe 240a that is fitted to the first area 200a; and a second pipe 240b that is fitted to the second area 200b. That is, the pipe 240 is provided over an entire area between the large diameter section 201 on the end 210 side and the large diameter section 201 on the end 220 side. Just as described, since the pipe 240 is provided over the entire area between the large diameter section 201 on the end 210 side and the large diameter section 201 on the end 220 side, the pipe 240 can firmly be fixed to the coil spring 200.

The coil spring 200 of this embodiment is provided with the first area 200a and the second area 200b as the areas with the different coil diameters between the large diameter section 201 on the end 210 side and the large diameter section 201 on the end 220 side. In this way, the pipe 240 is constructed of the first pipe 240a that corresponds to the first area 200a and the second pipe 240b that corresponds to the second area 200b. However, for example, like the coil spring 200 in the first embodiment, in the case where the coil diameter between the large diameter section 201 on the end 210 side and the large diameter section 201 on the end 220 side is constant, the single pipe 240 may be provided. Alternatively, even in the case where the coil diameter between the large diameter section 201 on the end 210 side and the large diameter section 201 on the end 220 side is not constant, a single pipe, an inner diameter of which varies or the like, may be used.

Figure 20:
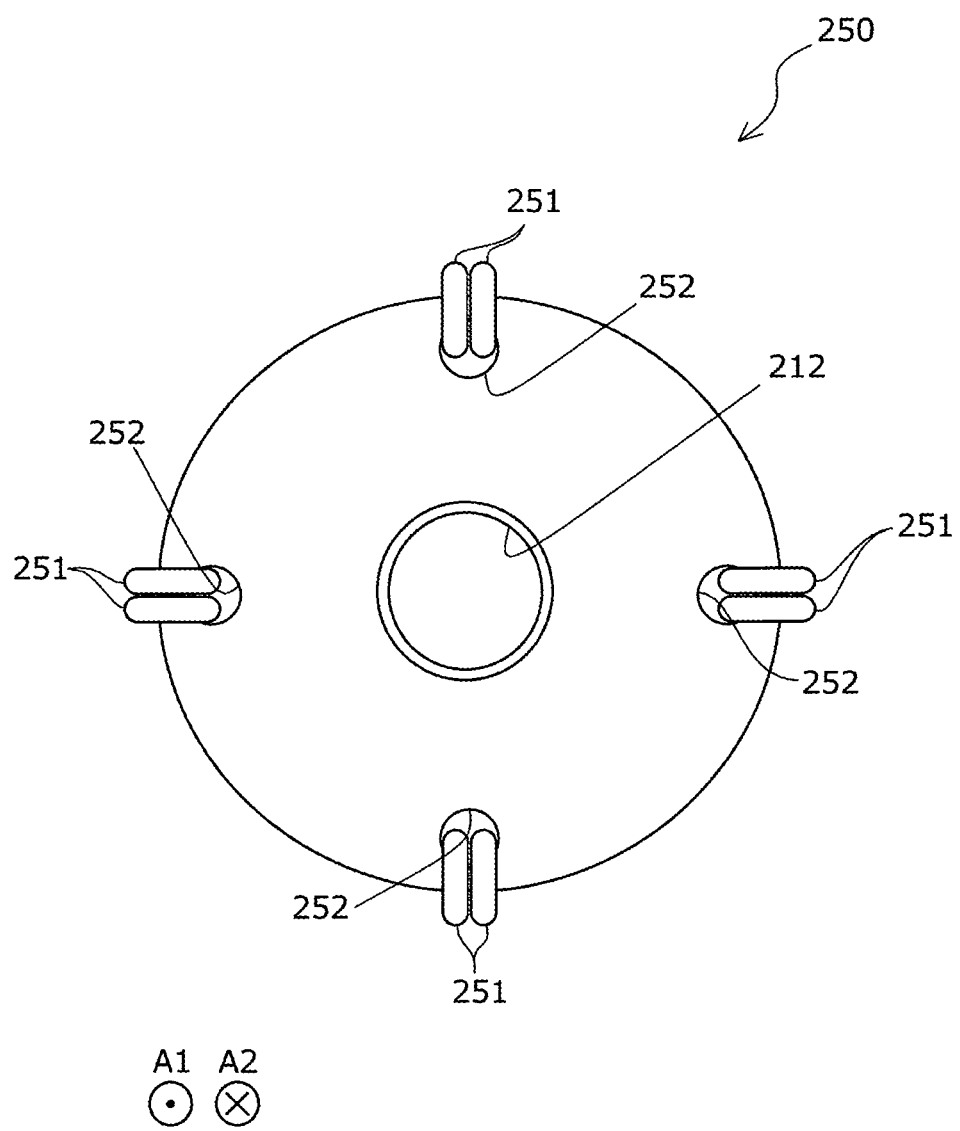
FIG. 20 is a schematic view in which an attachment/detachment section of an in-tube transit object according to a fifth embodiment of the present invention is seen in a winding-axis direction.
Figure 21:
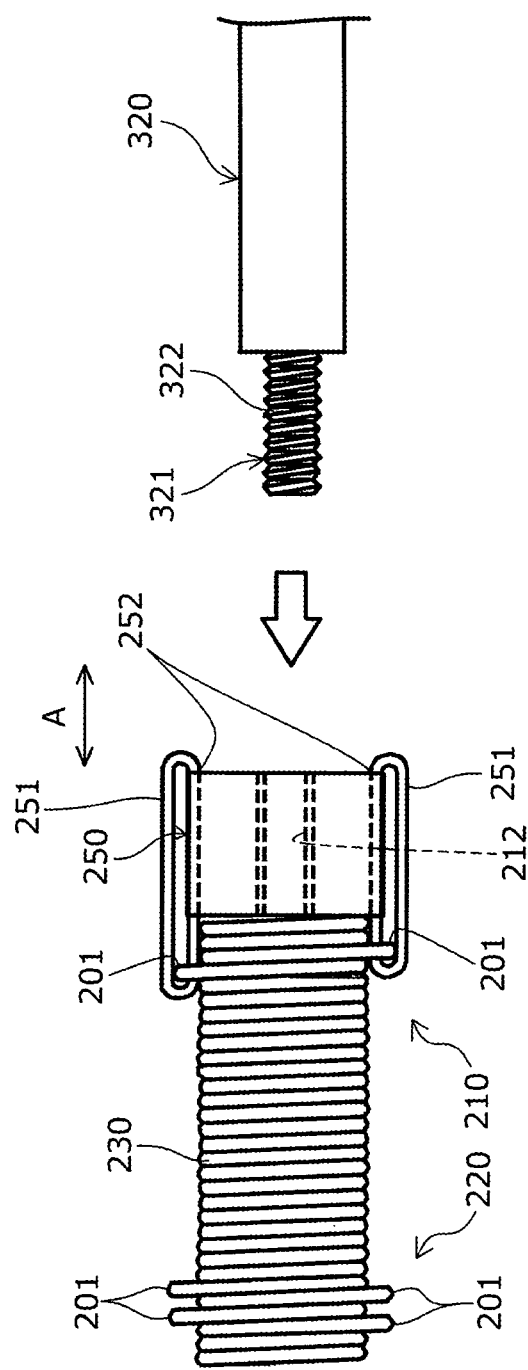
FIG. 21 is a schematic view in which the in-tube transit object according to the fifth embodiment of the present invention is seen in a direction that crosses the winding-axis direction.

[Fifth Embodiment] (FIG. 20 and FIG. 21)

Next, a description will be made on an in-tube transit object 1 according to a fifth embodiment with reference to FIG. 20 and FIG. 21. In FIG. 20 and FIG. 21, common components to those in the above first embodiment to fourth embodiment will be denoted by the same reference numerals, and the detailed description thereon will not be made. Here, the in-tube transit object 1 of this embodiment has similar characteristics to the in-tube transit objects 1 of the first embodiment to the fourth embodiment described above, and has a similar shape to the in-tube transit objects 1 of the first embodiment to the fourth embodiment except for portions, which will be described below.

As illustrated in FIG. 20 and FIG. 21, the in-tube transit object 1 of this embodiment has the attachment/detachment section 250 that is fixed to the coil spring 200 by a string-shaped member 251 and can be attached/detached to/from the wire 320 that is inserted in the catheter 300. The attachment/detachment section 250 is provided with a penetrating section 252 through which the string-shaped member 251 is inserted. When the string-shaped member 251 is inserted through the penetrating section 252 and is also inserted through the large diameter section 201 as the hole formed section, the attachment/detachment section 250 is fixed to the end 210 of the coil spring 200. The wire 320 has the rotatable male screw 322 in the tip portion 321, and the attachment/detachment section 250 has the female screw 212 corresponding to the male screw 322 therein. As illustrated in FIG. 21, the attachment/detachment section 250 is connected to the end 210 on the one side of the coil spring 200, and the wire 320 is connected to the attachment/detachment section 250 from an opposite side of the coil spring 200.

Just as described, the in-tube transit object 1 of this embodiment has the female screw 212 that corresponds to the male screw 322 of the wire 320, and also has the attachment/detachment section 250 that is fixed to the end 210 of the coil spring 200 by the string-shaped member 251 by using the large diameter section 201 as the hole formed section. Thus, the coil spring 200 of the in-tube transit object 1 in this embodiment can be attached/detached to/from the wire 320 by the attachment/detachment section 250 having high fitting accuracy to the wire 320 and having the simple configuration.

Here, in the in-tube transit object 1 of this embodiment, the string-shaped member 251 is formed from a palladium alloy. In other words, the string-shaped member 251 is formed by using the radiopaque material. Therefore, it is possible to improve visibility of the in-tube transit object 1 in this embodiment at the time when an X-ray is used at a medical site.

Figure 22:
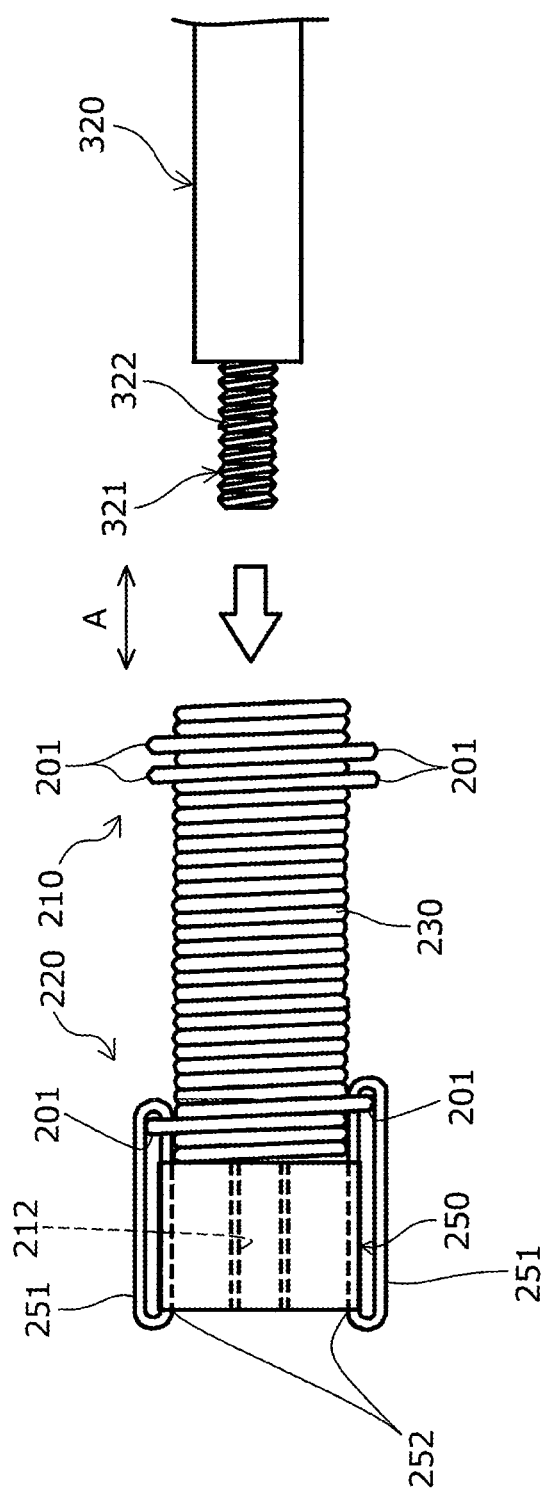
FIG. 22 is a schematic view in which an in-tube transit object according to a sixth embodiment of the present invention is seen in a direction that crosses a winding-axis direction.

[Sixth Embodiment] (FIG. 22)

Next, a description will be made on an in-tube transit object 1 according to a sixth embodiment with reference to FIG. 22. In FIG. 22, common components to those in the above first embodiment to fifth embodiment will be denoted by the same reference numerals, and the detailed description thereon will not be made. Here, the in-tube transit object 1 of this embodiment has similar characteristics to the in-tube transit objects 1 of the first embodiment to the fifth embodiment described above, and has a similar shape to the in-tube transit objects 1 of the first embodiment to the fifth embodiment except for portions, which will be described below.

As illustrated in FIG. 21, in the in-tube transit object 1 of the fifth embodiment, the attachment/detachment section 250 is connected to the end 210 on the one side of the coil spring 200, and the wire 320 is connected to the attachment/detachment section 250 from the opposite side of the coil spring 200. Meanwhile, in the in-tube transit object 1 of this embodiment, as illustrated in FIG. 22, the attachment/detachment section 250 is connected to the end 220 on the other side of the coil spring 200, and the wire 320 is inserted through the coil spring 200 from the end 210 on the one side to the end 220 on the other side and is connected to the attachment/detachment section 250. Thus, in the in-tube transit object 1 of this embodiment, the coil spring 200 is reinforced from the inside by the wire 320. Therefore, it is possible to suppress bending of the coil spring 200 in the catheter 300 and to improve an insertion property of the wire 320 in the catheter 300.

The present invention is not limited to the above embodiments, and various modifications can be made thereto within the scope of the invention described in the claims. It is needless to say that those fall within the scope of the present invention. For example, the coil spring 200 of the first embodiment includes two each of the large diameter sections 201 (the first large diameter sections 201A, the second large diameter sections 201B, the third large diameter sections 201C, and the fourth large diameter sections 201D) at the total of the eight positions at the end 210 on the direction A1 side and the end 220 on the direction A2 side so as to have the hole sections 202 in the four directions. However, the configuration of the coil spring 200 is not limited thereto. For example, the coil spring 200 may be configured to include the large diameter section 201 so as to have the hole section 202 in one to three directions or five directions or more. Alternatively, the coil spring 200 may be configured to include the large diameter section 201, which has the hole section 202 in each direction, at each position or three or more positions.

DESCRIPTION OF REFERENCE NUMERALS AND SYMBOLS

1: In-tube transit object
100: Cylindrical body (fiber section)
101: Wiring material (fiber)
103: Substantially center portion
110: First cylindrical section
120: Second cylindrical section
200: Coil spring (coil section)
200a: First area
200b: Second area
200d: Extended coil section
200e: End-side large diameter section
201: Large diameter section
201A: First large diameter section
201B: Second large diameter section
201C: Third large diameter section
201D: Fourth large diameter section
202: Hole section
210: End
212: Female screw
220: End
230: Element wire
240: Pipe (tubular section)
240a: First pipe
240b: Second pipe
250: Attachment/detachment section
300: Catheter (tube)
301: Tip
310: Inner wall (inside)
320: Wire
321: Tip portion
322: Male screw
400: Heart
410: Right atrium
420: Right ventricle
430: Left atrium
440: Left ventricle
450: Atrial septal
452: Defective hole

The invention claimed is:

1. An in-tube transit object that is inserted in a tube, the in-tube transit object comprising:
a coil section formed by winding an element wire; and
a fiber section attached to an end on one side and an end on the other side in a winding-axis direction of the coil section, wherein
the coil section is formed with hole formed sections, through each of which fiber of the fiber section is inserted, at the end on the one side and the end on the other side, and is inserted in an extending state in the winding-axis direction at the time when the in-tube transit object is inserted in the tube, and
the fiber section is configured to expand when seen in the winding-axis direction in the case where the in-tube transit object is inserted in the tube and then discharged from the tube, which brings the coil section into a compressed state in the winding-axis direction.

2. The in-tube transit object according to claim 1, wherein the hole formed section is a large diameter section that is formed by increasing a winding diameter of the element wire to be larger than winding diameters of the other portions in the coil section.

3. The in-tube transit object according to claim 2, wherein the coil section is formed with the large diameter section such that a hole section, through which the fiber is inserted, is formed at plural positions when the coil section is seen in the winding-axis direction.

4. The in-tube transit object according to claim 2, wherein the coil section is formed with the plural large diameter sections in a manner to overlap each other when the coil section is seen in the winding-axis direction.

5. The in-tube transit object according to any one of claim 1, wherein
the coil section is made of metal.

6. The in-tube transit object according to claim 5, wherein the coil section is made from an alloy containing nickel and titanium.

7. The in-tube transit object according to any one of claim 1, wherein
the tube is a catheter.

8. The in-tube transit object according to claim 7, wherein the coil section has an attachment/detachment section to/from a wire that is inserted through the catheter,
the wire has a rotatable male screw at a tip, and the attachment/detachment section has a female screw that is formed on inside of the coil section and corresponds to the male screw.

9. The in-tube transit object according to claim 8, wherein the attachment/detachment section has a tubular section that covers an outer circumference of the female screw.

10. The in-tube transit object according to claim 9, wherein
the tubular section covers the outer circumference of the female screw from the end on the one side to the end on the other side.

11. The in-tube transit object according to claim 7 further comprising:
an attachment/detachment section that is fixed to the coil section and can be attached/detached to/from a wire inserted through the catheter, wherein
the attachment/detachment section is provided with a penetrating section, through which a string-shaped member is inserted, and is fixed to the end of the coil section at the time when the string-shaped member is inserted through the penetrating section and is also inserted through the hole formed section,
the wire has a rotatable male screw at a tip, and
the attachment/detachment section has a female screw that corresponds to the male screw.

12. The in-tube transit object according to claim 11, wherein
the wire is inserted through the coil section from the end on the one side to the end on the other side and is connected to the attachment/detachment section.

13. The in-tube transit object according to claim 11, wherein
the string-shaped member is formed by using a radiopaque material.

14. The in-tube transit object according to claim 1, wherein
the fiber section is configured to expand at two positions on the end side on the one side and the end side on the other side when seen in the winding-axis direction in the case where the in-tube transit object is inserted in the tube and then discharged from the tube, which brings the coil section into the compressed state in the winding-axis direction.

\* \* \* \* \*